United States Patent
Tilley et al.

(10) Patent No.: US 9,458,185 B2
(45) Date of Patent: Oct. 4, 2016

(54) FIRST ROW METAL-BASED CATALYSTS FOR HYDOSILYLATION

(71) Applicant: THE REGENTS OF THE UNIVERSITY OF CALIFORNIA, Oakland, CA (US)

(72) Inventors: T. Don Tilley, Orinda, CA (US); Jian Yang, Houston, TX (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/377,833

(22) PCT Filed: Feb. 11, 2013

(86) PCT No.: PCT/US2013/025528
§ 371 (c)(1),
(2) Date: Aug. 8, 2014

(87) PCT Pub. No.: WO2013/120057
PCT Pub. Date: Aug. 15, 2013

(65) Prior Publication Data
US 2015/0353589 A1    Dec. 10, 2015

Related U.S. Application Data

(60) Provisional application No. 61/597,632, filed on Feb. 10, 2012.

(51) Int. Cl.
| | |
|---|---|
| *G07F 7/04* | (2006.01) |
| *C07F 15/04* | (2006.01) |
| *B01J 31/22* | (2006.01) |
| *B01J 31/18* | (2006.01) |
| *C07B 59/00* | (2006.01) |
| *C07F 7/08* | (2006.01) |

(52) U.S. Cl.
CPC .......... *C07F 15/045* (2013.01); *B01J 31/1895* (2013.01); *B01J 31/22* (2013.01); *B01J 31/2295* (2013.01); *C07B 59/004* (2013.01); *C07F 7/0809* (2013.01); *C07F 7/0829* (2013.01); *C07F 7/0896* (2013.01); *B01J 2231/323* (2013.01); *B01J 2531/847* (2013.01)

(58) Field of Classification Search
CPC ................................ C07F 15/04; B01J 31/18
USPC ............................................ 556/479; 546/10
See application file for complete search history.

(56) References Cited

U.S. PATENT DOCUMENTS

| | | |
|---|---|---|
| 3,970,850 A | 7/1976 | Jordan |
| 5,273,641 A | 12/1993 | Blechta et al. |
| 5,512,696 A | 4/1996 | Kreutzer et al. |
| 5,663,369 A | 9/1997 | Kreutzer et al. |
| 5,688,986 A | 11/1997 | Tam et al. |
| 5,821,378 A | 10/1998 | Foo et al. |
| 5,847,191 A | 12/1998 | Bunel et al. |
| 5,910,600 A | 6/1999 | Urata et al. |

FOREIGN PATENT DOCUMENTS

| | | |
|---|---|---|
| WO | WO 99/06357 | 2/1999 |
| WO | WO 2013/120057 | 8/2013 |

OTHER PUBLICATIONS

Lang et al., Inorganica Chimica Acta 361 (2008) 95-102.*
Leschke et al., Electrochimica Acta 48 (2003) 919-924.*
Over et al., Inorganic Chemistry, 2009, 48(10), 4317-4330.*
Albrecht and Van Koten, Angew. Chem., Int. Ed., 40, 3750-3781 (2001).
Bart, S. et al., J. Am, Chem. Soc., 126, 13794-13807 (2004).
Blankenstein and Pfaltz, Angew, Chem., 113:23, 4577-4579 (2001).
Braunstein, P. et al., Organometallics, 19, 2676-2683 (2000).
Brookhart and Grant, J. Am. Chem. Soc. 115, 2151-2156 (1993).
Chalk and Harrod, J. Am. Chem. Soc., 87:1, 16-21 (1965).
Chen, Y. et al., Organomeallics, 24, 149-155 (2005).
Christopher, R.E. et al., J. Chem. Soc. (A)., 205-2011 (1968).
Dieguez and Pamies, Accounts of Chemical Research, 43:2, 312-322 (2010).
Duckett and Perutz, Organometallics, 11, 90-98 (1992).
Fontaine, F. et al., Can. J. Chem., 81, 1299-1306 (2003).
Fryzuk, M., Can. J. Chem., 70, 2839-2845 (1992).
Glaser and Tilley, J. Am. Chem. Soc., 125, 13640-13641 (2003).
Hounjet, L., Inorg. Chem., 50, 5361-5378 (2011).
Hyder, I. et al., Dalton Trans., 3000-3009 (2007).
Jagt, R. et al., Organic Letters, 7:12, 2433-2435 (2005).
Kayaki, Y. et al., J. Org. Chem. 69, 2595-2597 (2004).
Kiso, Y. et al., Journal of Organometallic Chemistry, 50, 297-310 (1973).
Lang, H. et al., Inorganica Chimica Acta, 361, 95-102 (2008).
Lapointe, A. et al., J. Am, Chem. Soc., 119, 906-917 (1997).
Lang, H. et al., Z. Anorg. Allg. Chem., 629, 2371-2380 (2003).
Leschke, M. et al., Z. Anorg. Chem., 630, 2022-2030 (2004).
Leschke, M. et al., Electrochimica Acta, 48, 919-924 (2003).
Leschke, M. et al., Z. Anorg. Allg. Chem., 628, 349-356 (2002).
Lewis, L. et al, Platinum Metals Rev. 41, 66-75 (1997).

(Continued)

*Primary Examiner* — Porfirio Nazaroi Gonzalez
*Assistant Examiner* — Kofi Adzamli
(74) *Attorney, Agent, or Firm* — Morgan, Lewis & Bockius LLP; Jeffry S. Mann

(57) ABSTRACT

In various embodiments, the invention provides phosphine ligand supported first row metal catalysts with surprising and efficacious catalytic activity for hydrosilylation of pi-bonded substrates. Also provided are methods of using the catalysts of the invention to prepare hydrosilylated compounds.

10 Claims, 2 Drawing Sheets

(56) References Cited

OTHER PUBLICATIONS

Liu and Sandoval, Journal of Molecular Catalysis a: Chemical, 325, 65-72 (2010).
Maciejewski, H. et al., Journal of Organometallic Chemistry, 597, 175-181 (2000).
Maclachlan and Fryzuk, Organometallics, 24, 1112-1118 (2005).
Malda, H. et al., Organic Letters, 3:8, 1169-1171 (2001).
Martorell, A. et al., Tetrahedron: Asymmetry, 12, 2497-2499 (2001).
Minnaard, A. et al., Acc. Chem. Res,, 40, 1267-1277 (2007).
Monnereau, L., et al., Adv, Synth, Catal., 351, 1629-1636 (2009).
Moon and Lee, Journal of Organometallic Chemistry, 694, 473-477 (2009).
Nesmeyanov, A.N. et al., Tetrahedron, 17, 61-68 (1962).
Over, D. et al., Inorganic Chemistry, 48(10): 4317-4330 (2009).
Park, H. et al., Tetrahedron, 61, 6352-6367 (2005).
Peng, X. et al., Tetrahedron Letters, 49, 4862-4864 (2008).
Punji, B. et al., Dalton Trans., 1322-1330 (2006).
Reichel and Wrighton, Inorg. Chem., 19, 3858-3860 (1980).
Sangtrirutnugul and Tilley, Organometallics, 26, 5557-5568 (2007).
Speier, J. et al., J. Arm Chem. Soc., 79, 974-979 (1957).
Stradiotto, M. et al., Chem. Commun., 1200-1201 (2001).
Van Der Boom and Milstein, Chem. Rev., 103, 1759-1792 (2003).
Velder, J. et al., Adv. Synth. Catal., 1309-1315 (2008).
Wu, J. et al., J. Am. Chem. Soc., 132, 13214-13216 (2010).

\* cited by examiner

FIRST ROW METAL-BASED CATALYSTS FOR HYDOSILYLATION

STATEMENT OF GOVERNMENT RIGHTS

This invention was made with Government support under Grant No. CHE-0957106 awarded by The National Science Foundation. The Government has certain rights in this invention.

BACKGROUND OF THE INVENTION

The hydrosilylation of alkenes is a widely practiced catalytic transformation, and is of great importance for the production of organosilanes and materials based on poly(siloxane)s (Selected Reviews for Hydrosilylation: (a) Marciniec, B. in *Hydrosilylation: A Comprehensive Review on Recent Advances*; Marciniec, B., Eds., Springer, Netherlands, 2009, Chapter 1. (b) Troegel, D.; Stohrer, J. *Coord. Chem. Rev.* 2011, 255, 1440. (c) Roy, A. K. *Adv. Organomet. Chem.* 2008, 55, 1. (d) Marciniec, B. *Coord. Chem. Rev.* 2005, 249, 2374. (e) Ojima, I.; Li, Z.; Zhu, J. *The Chemistry of Organic Silicon Compounds*, Wiley: Avon, 1998; Chapter 29. (f) Marciniec, B.; Gulinski, J.; Urbaniak, W.; Kornetka, Z. W. *Comprehensive Handbook on Organosilicon Chemistry*; Pergamon: Oxford, 1992. (g) Lewis, L. N.; Stein, J.; Gao, Y.; Colborn, R. E.; Hutchins, G. *Platinum Metals Rev.* 1997, 41, 66-75. (d) Marciniec, B. In *Applied Homogeneous Catalysis with Organometallic Compounds*, second ed.; Cornils, B.; Herrmann, W. A., Eds., Wiley-VCH, Weinheim, 2002. (h) Reichl, J. A.; Berry, D. H. *Adv. Organomet. Chem.* 1999, 43, 197. (i) Roy, A. K. *Adv. Organomet. Chem.* 2008, 55, 1). For industrial applications, the most common and active hydrosilylation catalysts are based on platinum, and to a lesser degree other precious metals. Selective examples: (a) Speier, J. L.; Webster, J. A.; Barnes, G. H. *J. Am. Chem. Soc.* 1957, 79, 974. (b) Speier, J. L.; Hook, D. E. Dow Corning Corp., U.S. Pat. No. 2,823,218 A 1958. (c) Karstedt, B. D. General Electric Company, U.S. Pat. No. 3,775,452 A 1973. (d) Chalk, A. J.; Harrod, J. F. *J. Am. Chem. Soc.* 1965, 87, 16. (e) Seitz, F.; Wrighton, M. S. *Angew. Chem. Int. Ed. Engl.* 1988, 27, 289. (f) Duckett, S. B.; Perutz, R. N. *Organometallics* 1992, 11, 90. (g) LaPointe, A. M.; Rix, F. C.; Brookhart, M. *J. Am. Chem. Soc.* 1997, 119, 906. (h) Glaser, P. B.; Tilley, T. D. *J. Am. Chem. Soc.* 2003, 125, 13640. Due to the high cost associated with such metals, there is increasing interest in utilization of less expensive first-row transition metal catalysts for this transformation. Early examples of using first-row transition metal carbonyl compounds for hydrosilylation catalysis under high temperature or photo irradiation conditions: (a) Nesmeyanov, A. N.; Freidlina, R. K.; Chukovskaya, E. C.; Petrova, R. G.; Belyaysky, A. B. *Tetrahedron* 1962, 17, 61; (b) Reichel, C. L.; Wrighton, M. S. *Inorg. Chem.* 1980, 19, 3858. There has been some progress toward this goal, including the work of Brookhart and coworkers on the cationic Cp*Co system for the catalytic hydrosilylation of 1-hexene with $Et_3SiH$ (Brookhart, M.; Grant, B. E. *J. Am. Chem. Soc.* 1993, 115, 2151). In addition, Chirik et al. have reported neutral bis(imino)pyridine iron bis(dinitrogen) complexes as catalyst precursors for the hydrosilylation of a variety of alkenes with $PhSiH_3$ (hydrosilylations with $Ph_2SiH_2$ appear to be much slower) ((a) Bart, S. C.; Lobkovsky, E.; Chirik, P. J. *J. Am. Chem. Soc.* 2004, 126, 13794; (b) Delis, J. G. P.; Chirik, P. J.; Tondreau, A. M. Momentive Performance Materials Inc., U.S. Pat. No. 0,009,565 A1 2011; (c) For a recent report on Fe-catalyzed regioselective diene hydrosilylation: Wu, J. Y.; Stanzl, B. N.; Ritter, T. *J. Am. Chem. Soc.* 2010, 132, 13214). Catalytic systems based on indenyl nickel complexes have also been reported for the regioselective hydrosilylation of styrene with $PhSiH_3$ ((a) Fontaine, F.-G.; Nguyen, R.-V.; Zargarian, D. *Can. J. Chem.* 2003, 81, 1299; (b) Chen, Y.; Sui-Seng, C.; Boucher, S.; Zargarian, D. *Organometallics* 2005, 24, 149: Hyder, I.; Jimenez-Tenorio, M.; Puerta, M. C.; Valerga, P. *J. Chem. Soc. Dalton Trans.* 2007, 3000). Other nickel(II) and nickel(0) complexes such as $[Ni(PPh_3)_2Cl_2]$ and $[\{Ni(\eta\text{-}CH_2\!=\!CHSiMe_2)_2O\}_2\{\mu\text{-}(\eta\text{-}CH_2\!=\!CHSiMe_2)_2O\}]$ exhibit activity toward hydrosilylation, but these reactions are typically associated with harsh reaction conditions or limited substrate scope, and often mediate extensive dehydrosilylation (Marciniec, B.; Maciejewski, H.; Kownacki, I. *J. Organomet. Chem.* 2000, 597, 175) and/or silane redistribution ((a) Kiso, Y.; Kumada, M.; Tamao, K.; Umeno, M. *J. Organomet. Chem.* 1973, 50, 297; (b) Kiso, Y.; Kumada, M.; Maeda, K.; Sumitami, K.; Tamao, K. *J. Organomet. Chem.* 1973, 50, 311) as processes that compete with hydrosilylation. Thus, the development of generally effective and useful alkene hydrosilylations using first-row metals such as manganese, iron, cobalt and nickel is still at a very early stage.

There are several industrially important catalytic processes employing phosphorus ligands. For example, U.S. Pat. No. 5,910,600 to Urata, et al. discloses that bisphosphite compounds can be used as a constituting element of a homogeneous metal catalyst for various reactions such as hydrogenation, hydroformylation, hydrocyanation, hydrocarboxylation, hydroamidation, hydroesterification and aldol condensation.

U.S. Pat. No. 5,512,696 to Kreutzer, et al. discloses a hydrocyanation process using a multidentate phosphite ligand, and the patents and publications referenced therein describe hydrocyanation catalyst systems pertaining to the hydrocyanation of thylenically unsaturated compounds. U.S. Pat. Nos. 5,723,641, 5,663,369, 5,688,986 and 5,847,191 disclose processes using zero-valent nickel and multidentate phosphite ligands.

U.S. Pat. No. 5,821,378 to Foo, et al. discloses reactions that are carried out in the presence of zero-valent nickel and a multidentate phosphite ligand. PCT Application WO99/06357 discloses multidentate phosphite ligands having alkyl ether substituents on the carbon attached to the ortho position of the terminal phenol group.

Though first row metals supported on phosphorus-based ligands are known to have catalytic activity, such compounds have not been applied to the hydrosilyation of pi-bonded species.

Hydrosilylation reactions are recognized high-value reactions in industry and in the laboratory. Currently, industrially relevant hydrosilylation reactions are performed utilizing precious metal-based catalysts. Hydrosilylation catalysts based on first-row metals would provide entry into valuable hydrosilylated compounds in a cost-effective manner. Moreover, the use of certain first-row metals presents the opportunity to perform hydrosilylation using environmentally friendly catalysts (e.g., Fe-based). The present invention provides such catalysts.

The introduction of cationic first row metal compounds, which are effective, general catalysts for the hydrosilylation of alkenes and other pi-bonded species would provide a significant advance in the art. Quite surprisingly, the present invention provides such catalysts and method of using these catalysts to effect hydrosilylation across pi-bonds.

BRIEF SUMMARY OF THE INVENTION

In various embodiments, the present invention provides compounds, which are cationic first row metal species supported on at least one phosphine ligand. Exemplary cationic species of the invention are effective hydrosilylation compounds. Exemplary metals of use in the catalysts of the invention include nickel, cobalt, copper and iron. In an exemplary embodiment, the cationic species of the invention is a nickel compound. Exemplary metal compounds, e.g., cationic metal compounds, e.g., cationic nickel compounds of the invention are catalysts for hydrosilylation.

The catalysts of the invention provide numerous advantages. For example, the catalysts based upon first-row metals are economically attractive when compared to the current precious metal-based hydrosilylation catalysts. The catalysts of the invention provide entry into synthetic routes providing excellent yields of hydrosilylation products at low catalyst loading and moderate reaction temperature. Furthermore, exemplary catalysts of the invention display a unique reactivity, e.g., with exemplary catalysts, secondary hydrosilanes are more readily added across pi-bonds than other hydrosilanes. Furthermore, the preparation of the ligands from readily available and easily variable reagents provides for a series of ligands that are electronically, sterically and stereochemically tunable, which, in turn, are of use to prepare a series of catalysts with readily tunable properties.

An exemplary ligand of use in the compounds of the invention includes a phosphorus donor atom and a nitrogen donor atom. In various embodiments, the invention provides a cationic first row metal compound in which the metal is supported by at least one phosphine ligand having a phosphorus donor atom and a nitrogen donor atom. In various embodiments, the invention provides a first row metal compound having a phosphine ligand with Formula I:

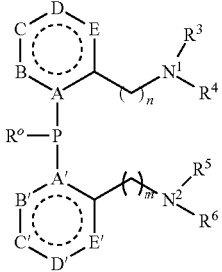

(I)

in which $R^o$ is a substituted or unsubstituted alkyl or heteroalkyl moiety, an amine, or a substituted or unsubstituted aryl or heteroaryl moiety (e.g., a substituted or unsubstituted aryloxy or heteroaryloxy moiety). A, A', B, B' C, C', D, D', E and E' are each independently selected from $CR^7$ and N. When a ligand of a compound of the invention includes more than one $CR^7$ moiety, each $R^7$ moiety is independently selected from those substituents referred to herein as "aryl group substituents". $R^0$ is a substituted or unsubstituted alkyl or heteroalkyl moiety, an amine, or a substituted or unsubstituted aryl or heteroaryl moiety (e.g., a substituted or unsubstituted aryloxy or heteroaryloxy moiety). The indices m and n are integers independently selected from 0, 1, 2 and 3. The radicals, $R^3$, $R^4$, $R^5$ and $R^6$ are independently selected from H, substituted or unsubstituted alkyl, and substituted or unsubstituted heteroalkyl. $R^3$ and $R^4$ or $R^5$ and $R^6$ are optionally joined, together with the nitrogen atom to which they are attached to form a ring, which is a member selected from substituted or unsubstituted heteroalkyl with), 1 or 2 degrees of unsaturation and substituted or unsubstituted heteroaryl having five or six members; in exemplary embodiments, the ring so formed is fused to the ring formed from moieties A-E or A'-E', respectively. In various embodiments, the $R^3$ is bonded to E. In various embodiments, $R^6$ is bonded to E'. In various embodiments, a first and a second ring are formed by bonds between $R^3$ and E and $R^6$ and E', respectively. In exemplary embodiments, one or both of the nitrogen atoms and the phosphorus atom bond the metal atom through one or two M-N and a M-P bond, respectively.

When the first row metal is supported on the ligand, an exemplary resulting compound is a cation and includes an anionic moiety, $Y^-$, which is an organic or inorganic anion. In an exemplary embodiment, $Y^-$ is $B(C_6F_5)_4$. In various embodiments, the cationic compound of the invention is a catalyst for the addition of a hydrosilane across a pi-bonded system.

In various embodiments, the invention provides new first row metal catalysts for hydrosilylation in which tridentate ligands containing a central, strong donor atom support the metal. Such ligands promote stability for the catalytic center, and provide a compounds with high reactivity toward substrate activations.[9] Exemplary ligands in the compounds of the invention are modeled on bis(8-quinolyl)silyl (NSiN) complexes[10]. In various embodiments, the central anionic silyl group of the NSiN ligand is replaced by a neutral phosphorus donor. The resulting bis(8-quinolyl)phosphinyl (NPN) ligand combines a soft, strong donor and two hard, hemilabile quinolyl groups in a chelating scaffold and promotes catalytic bond activations.

Thus, in an exemplary embodiment, the invention provides a first row metal compound having a ligand with Formula II:

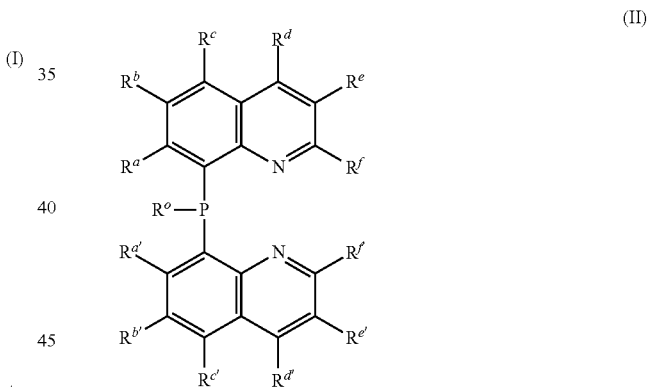

(II)

in which $R^a$, $R^b$, $R^c$, $R^d$, $R^e$, $R^f$, $R^{a'}$, $R^{b'}$, $R^{c'}$, $R^{d'}$, $R^{e'}$, and $R^{f'}$ are each members independently selected from those moieties referred to herein as "aryl group substituents".

In various embodiments, $R^0$ is a substituted or unsubstituted alkyl or heteroalkyl moiety, an amine, or a substituted or unsubstituted aryl or heteroaryl moiety (e.g., a substituted or unsubstituted aryloxy or heteroaryloxy moiety). In an exemplary embodiment, the substituted aryloxy moiety has the formula:

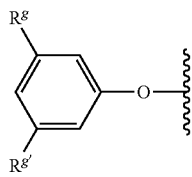

in which $R^g$ and $R^{g'}$ are independently selected from those moieties referred to herein as "aryl group substituents".

In an exemplary embodiment, the invention provides first row metal complexes (e.g., nickel) complexes of the bis(8-quinolyl)(3,5-di-tert-butylphenoxy)phosphine ligand, which are effective general catalysts for hydrosilylation of alkenes.

Also provided by the instant invention are first row metal compound precursors to the catalysts of the invention. In various embodiments, these precursors are neutral metal complexes with the ligand. In an exemplary embodiment, the ligand includes a phosphorus and a nitrogen donor atom, e.g., a ligand of Formula I and Formula II. The neutral metal complexes include at least one abstractable moiety (e.g., an electronegative donor atom or group, e.g., halide, alkoxide, carboxylate, acac, amido, etc.). The abstractable group can also be one removable by deprotonation, e.g., alkyl or aryl. Other abstractable groups and methods to remove such groups from a neutral metal complex of the invention will be apparent to those of skill in the art.

The present invention also provides a method of preparing a first row metal compound of the invention from a precursor. The method includes contacting the precursor with a reactive species capable of abstracting at least one abstractable moiety from the precursor, thereby forming a ligand-supported cationic metal species of the invention. Exemplary compounds of the invention catalyze the addition of a hydrosilane across a pi-bonded system. Exemplary reactive species of use in the method include a moiety that produces a counterion for the resulting cationic first row metal compound. In an exemplary embodiment, the abstractable moiety is halogen (e.g., chloro). In an exemplary embodiment, the reactive species is $Li(OEt_2)_3[B(C_6F_5)_4]$.

In various embodiments, the invention provides a method of hydrosilylating a pi-bonded system, such as an alkene, an alkyne, or a carbonyl. The method includes contacting a molecule including the pi-bonded system with a catalyst of the invention and a hydrosilane under conditions appropriate to accomplish the hydrosilylation of the pi-bonded system, thereby forming a hydrosilylated compound.

These and other embodiments, objects and advantages of the subject invention will readily occur to those of skill in the art in view of the disclosure herein.

DETAILED DESCRIPTION OF THE INVENTION

I. Introduction

Figure 1:
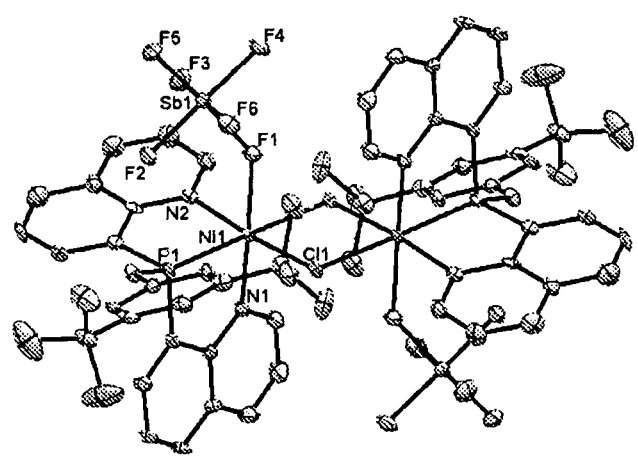
FIG. 1 is an ORTEP drawing of the X-ray crystal structure of 3b. Hydrogen atoms and $C_6H_5F$ are omitted for clarity. Key bond distances (Å): Ni(1)-N(1)=2.092(6), Ni(1)-N(2)=2.070(7), Ni(1)-P(1)=2.347(2), Ni(1)-F(1)=2.262(4), Sb(1)-F(1)=1.904(4), Sb(1)-F(2)=1.873(5), Sb(1)-F(3)=1.877(5), Sb(1)-F(4)=1.874(5), Sb(1)-F(5)=1.867(5), Sb(1)-F(6)=1.869(5).
Figure 2:
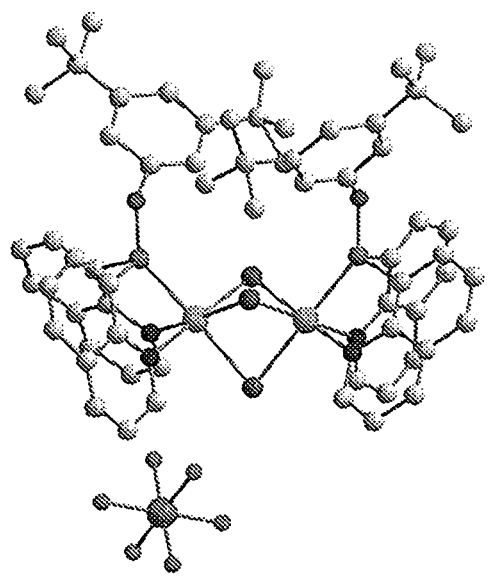
FIG. 2 is the molecular structure of 4b. Hydrogen atoms are omitted for clarity.

Aspects of the invention include cationic first row metal (e.g., nickel) compounds in which the metal atom is supported on one or more phosphorus-containing ligands through at least a donor phosphorus atom. Exemplary compounds of the invention are soluble in one or more organic solvent. In various embodiments, the cationic first row metal compounds of the invention are catalysts for hydrosilylation of pi-bonded systems. Also provided are precursors to such catalytic metal compounds, which are readily converted to active catalysts. The invention also provides methods of performing hydrosilyilation of a pi-bonded system using one or more catalyst of the invention.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

In describing the present invention, the following terms will be employed, and are intended to be defined as indicated below.

II. Definitions

As used in this specification and the appended claims, the singular forms "a", "an" and "the" include plural referents unless the content explicitly dictates otherwise. Thus, for example, reference to "cationic nickel catalyst" includes a mixture of two or more such compounds, and the like.

Where substituent groups are specified by their conventional chemical formulae, written from left to right, the structures optionally also encompass the chemically identical substituents, which would result from writing the structure from right to left, e.g., —CH$_2$O— is intended to also recite —OCH$_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di-, tri- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to optionally include those derivatives of alkyl defined in more detail below, such as "heteroalkyl." Alkyl groups that are limited to hydrocarbon groups are termed "homoalkyl". Exemplary alkyl groups include the monounsaturated $C_{9-10}$, oleoyl chain or the diunsaturated $C_{9-10, 12-13}$ linoeyl chain.

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The terms "aryloxy" and "heteroaryloxy" are used in their conventional sense, and refer to those aryl or heteroaryl groups attached to the remainder of the molecule via an oxygen atom.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —CO$_2$R'— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Further exemplary cycloalkyl groups include steroids, e.g., cholesterol and its derivatives. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxyl)propyl, and the like).

Each of the above terms (e.g., "alkyl," "heteroalkyl," "aryl" and "heteroaryl") are meant to optionally include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: H, substituted or unsubstituted aryl, substituted or unsubstituted heteroaryl, substituted or unsubstituted heterocycloalkyl, —OR', =O, =NR', =N—OR', —NR'R", —SR', halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR", —NR—C(NR'R")=NR"', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R"' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). These terms encompass groups considered exemplary "alkyl group substituents", which are components of exemplary "substituted alkyl" and "substituted heteroalkyl" moieties.

Similar to the substituents described for the alkyl radical, substituents for the aryl and heteroaryl groups are generically referred to as "aryl group substituents." The substituents are selected from, for example: H, substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present.

Two of the substituents on adjacent atoms of the aryl or heteroaryl ring may optionally be replaced with a substituent of the formula -T-C(O)—(CRR')$_q$-U-, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R"')$_d$—, where s and d are independently integers of from 0 to 3, and X is —O—, —NR'—, —S—, —S(O)—, —S(O)$_2$—, or —S(O)$_2$NR'—. The substituents R, R', R" and R"' are preferably independently selected from hydrogen or substituted or unsubstituted (C$_1$-C$_6$)alkyl. These terms encompass groups considered exemplary "aryl group substituents", which are components of exemplary "substituted aryl" and "substituted heteroaryl" moieties.

As used herein, the term "acyl" describes a substituent containing a carbonyl residue, C(O)R. Exemplary species for R include H, halogen, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems may include aromatic as well as non aromatic rings. Examples of "fused ring systems" are naphthalenes, indoles, quinolines, chromenes and the like.

As used herein, the term "heteroatom" includes oxygen (O), nitrogen (N), sulfur (S) and silicon (Si) and boron (B).

The symbol "R" is a general abbreviation that represents a substituent group that is selected from H, substituted or unsubstituted alkyl, substituted or unsubstituted heteroalkyl, substituted or unsubstituted aryl, substituted or unsubstituted heteroaryl, and substituted or unsubstituted heterocycloalkyl groups.

The term "ligand" has the meaning ordinarily ascribed to it in the art. Exemplary ligands include at least one donor atom capable of binding to a first row metal. Ligands can include sterically bulky species, such as substituted or unsubstituted aryl, substituted or unsubstituted heteroaryl and substituted or unsubstituted fused ring systems, secondary and tertiary alkyl groups and the like. As described below, a ligand of use in the invention can be conceptualized as including a linker joining two or more donor atoms, which are the same or different atoms.

The term "salt(s)" includes salts of the compounds prepared by the neutralization of acids or bases, depending on the particular ligands or substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Certain specific compounds of the present invention contain both basic and acidic functionalities that allow the compounds to be converted into either base or acid addition salts. Hydrates of the salts are also included. An exemplary salt of the invention includes a boron-containing anion, e.g., $B(C_6F_5)_4$.

Certain compounds of the present invention possess asymmetric carbon atoms (optical centers) or double bonds; the racemates, diastereomers, geometric isomers and individual isomers are encompassed within the scope of the present invention. Optically active (R)- and (S)-isomers and d and l isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are included.

The compounds disclosed herein may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

Below are examples of specific embodiments for carrying out the present invention. The examples are offered for illustrative purposes only, and are not intended to limit the scope of the present invention in any way.

III. The Compositions a. The Compounds

In various embodiments, the present invention provides cationic compounds of first row metal atoms supported on a phosphorus-containing ligand. Exemplary first row metal atoms include, without limitation, nickel, cobalt, copper and iron. The metal is optionally further bound to at least one, two or more additional ligands in addition to the phosphorus-containing ligand. Examples of such additional ligands include, e.g., an electronegative donor atom or group, e.g., halide, alkoxide, carboxylate, acac, amido, etc. The abstractable group can also be removable by deprotonation, e.g., alkyl or aryl. The structure of the phosphorus-containing ligand is readily varied depending on the desired properties (e.g., stability, reactivity, substrate selectivity, etc.) of the compound of the invention. Variation of the ligand allows the properties of the compound to be tuned including, without limitation, its size, shape, hydrophilicity, hydrophobicity, electronic distribution, and stereochemistry.

In various embodiments, the cationic first row metal species is an effective hydrosilylation catalyst, adding the elements of a hydrosilane across a pi-bonded system, e.g., alkene, alkyne, carbonyl and the like. In an exemplary embodiment, the cationic species of the invention is a nickel compound. Exemplary cationic nickel compounds of the invention are catalysts for hydrosilylation.

The catalysts of the invention provide numerous advantages. For example, the catalysts, based upon first-row metals are economically attractive when compared to precious metal catalysts. The catalysts provide excellent yields of hydrosilylation products at low catalyst loading and moderate reaction temperature. Furthermore, exemplary catalysts of the invention display a unique reactivity, e.g., with exemplary catalysts, secondary silanes are more readily added across pi-bonds than other silanes. Furthermore, the preparation of the ligands from readily available and easily variable reagents provides for a series of ligands with tunable properties, which, in turn, are of use to prepare a series of catalysts that are readily tunable.

An exemplary ligand of use in the compounds of the invention includes a phosphorus donor atom and a nitrogen donor atom. In various embodiments, the invention provides a cationic first row metal compound in which the metal is supported by at least one phosphine ligand. In various embodiments, the invention provides a first row metal compound having a ligand with Formula I:

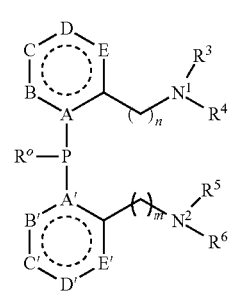

(I)

in which A, A', B, B' C, C', D, D', E and E' are each independently selected from $CR^7$ and N. When a ligand of a compound of the invention includes more than one $CR^7$ moiety, each $R^7$ moiety is independently selected from those substituents referred to herein as "aryl group substituents". $R^o$ is a substituted or unsubstituted alkyl or heteroalkyl moiety, an amine, or a substituted or unsubstituted aryl or heteroaryl moiety (e.g., a substituted or unsubstituted aryloxy or heteroaryloxy moiety). The indices m and n are integers independently selected from 0, 1, 2 and 3. $R^o$ is as described above. The radicals, $R^3$, $R^4$, $R^5$ and $R^6$ are independently selected from H, substituted or unsubstituted alkyl, and substituted or unsubstituted heteroalkyl. $R^3$ and $R^4$ or $R^5$ and $R^6$ are optionally joined, together with the nitrogen atom to which they are attached to form a ring, which is a member selected from substituted or unsubstituted heteroalkyl and substituted or unsubstituted heteroaryl having five or six members; in exemplary embodiments, the ring so formed is fused to the ring formed from moieties A-E or A'-E', respectively. In various embodiments, the $R^3$ group is bonded to E. In various embodiments, $R^6$ is bonded to E'. In various embodiments, a first and a second ring are formed by bonds between $R^3$ and E and $R^6$ and E', respectively. In the embodiments in which a ring is formed by joining $R^3$ to E and/or $R^6$ to E', one or both of the rings so formed are substituted or unsubstituted heteroaryl rings. The rings formed by atoms A-E and A'-E' are independently selected from substituted or unsubstituted aryl and substituted or unsubstituted heteroaryl rings.

In exemplary embodiments, each $R^7$ is independently selected from H, substituted or unsubstituted alkyl, substituted or unsubstituted heteroalkyl, halogen, CN, $CF_3$, acyl, $-SO_2NR^8R^9$, $-NR^8R^9$, $-OR^8$, $-S(O)_2R^8$, $-C(O)R^9$, $-COOR^8$, $-OC(O)R^8$, $-C(O)NR^8R^9$, $-NR^8C(O)R^9$, $-NR^8SO_2R^9$ and $-NO_2$.

Exemplary moieties for $R^8$ and $R^9$ include members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^8$ and $R^9$, together with the atoms to which they are bonded, are optionally joined to form a 5- to 7-membered ring, which is a member selected from substituted or unsubstituted cycloalkyl, substituted or unsubstituted heterocycloalkyl, substituted or unsubstituted aryl and substituted or unsubstituted heteroaryl.

In various embodiments, the invention provides compounds based on exemplary ligands modeled on bis(8-quinolyl)silyl (NSiN) ligands. In various embodiments, the central anionic silyl group of the NSiN ligand is replaced by a neutral phosphorus donor. The resulting bis(8-quinolyl) phosphinyl (NPN) ligand combines a soft, strong donor and two hard, hemilabile quinolyl groups in a chelating scaffold and promotes catalytic bond activations.

When the first row metal is supported on the ligand, an exemplary resulting compound is a cation and includes an anionic moiety, $Y^-$, which is an organic or inorganic anion. In an exemplary embodiment, $Y^-$ is $B(C_6F_5)_4$. In various embodiments, the cationic compound of the invention is a catalyst for the addition of a hydrosilane across a pi-bonded system.

In various embodiments, the invention provides new first row metal catalysts for hydrosilylation in which tridentate ligands containing a central, strong donor atom support the metal. Such ligands promote stability for the catalytic center, and provide a compounds with high reactivity toward substrate activations ((a) van der Boom, M. E.; Milstein, D. *Chem. Rev.* 2003, 103, 1759; (b) Albrecht, M.; van Koten, G. *Angew. Chem. Int. Ed.* 2001, 40, 3750; (c) Ozerov, O. V. in *The Chemistry of Pincer Compounds*; Morales-Morales, D.; Jensen, C., Eds.; Elsevier Science: Amsterdam, 2007, Chapter 13, p 287; (d) Fryzuk, M. D. *Can. J. Chem.* 1992, 70, 2839). Exemplary ligands in the compounds of the invention are modeled on bis(8-quinolyl)silyl (NSiN) complexes ((a) Stradiotto, M.; Fujdala, K.; Tilley, T. D. *Chem. Commun.* 2001, 13, 1200; (b) Sangtrirutnugul, P.; Tilley, T. D. *Organometallics* 2007, 26, 5557. (c) Sangtrirutnugul, P. PhD thesis, UC Berkeley, USA, 2007). In various embodiments, the central anionic silyl group of the NSiN ligand is replaced by a neutral phosphorus donor. The resulting bis(8-quinolyl) phosphinyl (NPN) ligand combines a soft, strong donor and two hard, hemilabile quinolyl groups in a chelating scaffold and promotes catalytic bond activations.

In an exemplary embodiment, the invention provides a first row metal compound having a ligand with Formula II:

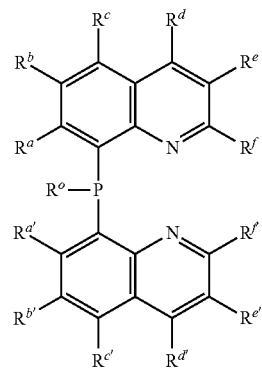

(II)

in which $R^a$, $R^b$, $R^c$, $R^d$, $R^e$, $R^f$, $R^{a'}$, $R^{b'}$, $R^{c'}$, $R^{d'}$, $R^{e'}$, and $R^{f'}$ are each members independently selected from those moieties referred to herein as $R^7$.

In various embodiments, $R^o$ is a substituted or unsubstituted alkyl or heteroalkyl moiety, an amine, or a substituted or unsubstituted aryl or heteroaryl moiety (e.g., a substituted or unsubstituted aryloxy or heteroaryloxy moiety). In an exemplary embodiment, the substituted aryloxy moiety has the formula:

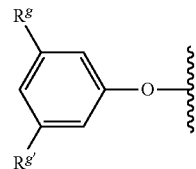

in which $R^g$ and $R^{g'}$ are independently selected from those moieties referred to herein as "aryl group substituents". In an exemplary embodiment, each of $R^g$ and $R^{g'}$ are independently selected from those groups referred to herein as $R^7$.

In an exemplary embodiment, the invention provides first row metal complexes (e.g., nickel) complexes of the bis(8-quinolyl)(3,5-di-tert-butylphenoxy)phosphine ligand, which are effective general catalysts for hydrosilylation of alkenes.

In an exemplary embodiment, the invention provides a precursor to a cationic metal complex of the invention. In various embodiments, these precursor is a neutral metal complex with the ligand. The neutral metal complex includes at least one abstractable moiety (e.g., an electronegative donor atom or group, e.g., halide, alkoxide, carboxylate, acac, amido, etc.). The abstractable group can also be one removable by deprotonation, e.g., alkyl or aryl. Other abstractable groups and methods to remove such groups from a neutral metal complex of the invention will be apparent to those of skill in the art.

An exemplary precursor of the invention has the formula:

I-M(X)$_s$ in which I is a compound according to Formula I, M is a metal, X is an abstractable ligand for the metal and s is an integer selected from 0, 1, 2, 3 and 4.

In an exemplary embodiment, the precursor of the invention has the formula:

II-M(X)$_s$ in which II is a ligand according to Formula II, and M, X and s are as described above.

In an exemplary embodiment, the invention provides a cationic metal-ligand compound having the general formula:

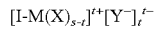

in which I is a ligand according to Formula I. M is a first row metal atom. X is a ligand for the metal. Y⁻ is an anion. The indeces s and t are integers selected from 0, 1, 2, 3 and 4 and are selected such that s-t is 0, 1, 2 or 3. As will be understood by those of skill in the art, in those embodiments in which the compound is a cationic species, an appropriate anion is present in the compound as is discussed in greater detail herein.

In an exemplary embodiment, the invention provides a cationic metal-ligand compound having the general formula:

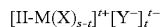

in which II is a ligand according to Formula II. M, X, Y⁻, s and t as described above.

In various embodiments, the compound of the invention is a catalyst for the addition of a hydrosilane across a pi-bonded system.

As noted above, in various aspects, the invention provides a compound that includes a first row metal atom supported by one or more ligand, e.g., a phosphine ligand. In exemplary embodiments, a ligand of use in the present compositions is a multidentate ligand, including 2, 3, 4 or more donor atoms. In various compounds of the invention, the ligand is rigid (e.g., a ring structure) and is robust under a variety of chemical conditions (e.g., those utilized for hydrosilylation of pi-bonded organic substrates). Exemplary ligands include one or more moiety on which the pattern of substitution and/or the nature of the substituents is readily varied (e.g., an aryl or heteroaryl moiety), which allows for the facile modification of the electronic properties of the ligand and provides a route to the tune the electronic properties of the compositions of the invention to induce, optimize, minimize or prevent a particular type of reaction mediated by the composition of the invention. Furthermore, the ease of engineering a composition of the invention allows for the design of a catalyst that functions optimally with a selected substrate or class of substrates (e.g., primary, secondary or tertiary hydrosilanes, substituted or unsubstituted alkenes, substituted or unsubstituted alkynes, carbonyl-containing compounds and the like).

Exemplary ligands of use in the present invention include those with a phosphorus donor atom, for example:

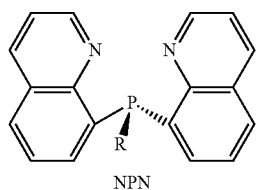

NPN

R = ᵗBu, NMe₂, Ph, OPh,
OAr^{tBu} (Ar^{tBu} = 3,5-ᵗBu₂C₆H₃),
OAr_F (Ar_F = 3,5-(CF₃)₂C₆H₃), etc.

Further, specific examples of ligand species of use in the compounds of the invention include:

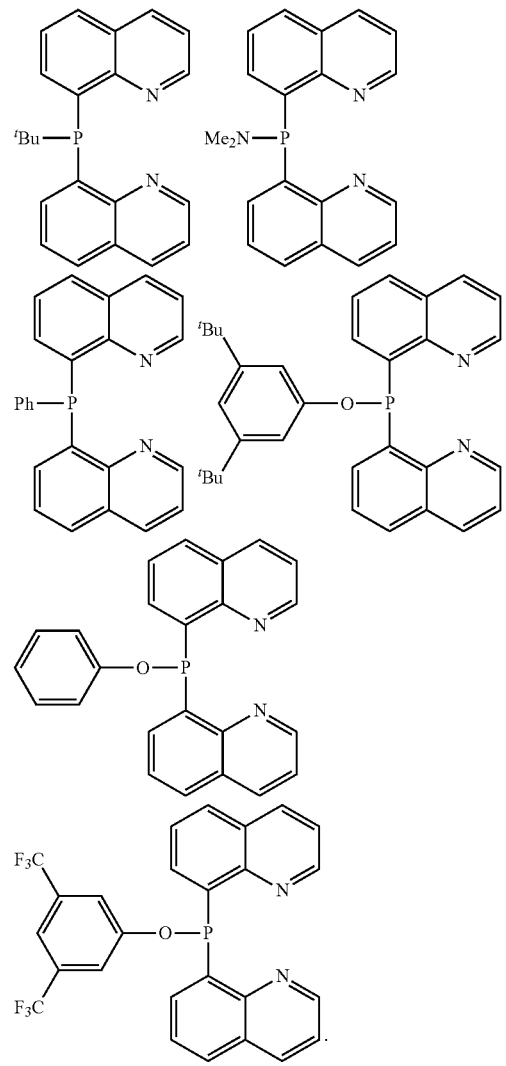

In an exemplary embodiment, the invention provides first row metal complexes (e.g., nickel) complexes of the bis(8-quinolyl)(3,5-di-tert-butylphenoxy)phosphine ligand, which are effective general catalysts for hydrosilylation of alkenes.

The composition of the invention is exemplified herein by reference to species in which the ligand is a phosphorus-containing ligand. In an exemplary embodiment, a phosphorus atom of the ligand is a donor atom for the first row metal species. Exemplary ligands include both a donor phosphorus atom and a donor nitrogen atom. Those of skill in the art will recognize that this focus is for clarity of illustration and other ligands have utility as well.

Phosphorus-containing ligands are ubiquitous ligands in catalysis and are used for a number of commercially important chemical transformations. Phosphorus-containing ligands commonly encountered in catalysis include phosphines and phosphites. Monophosphine and monophosphite ligands are compounds that contain a single phosphorus atom that serves as a donor to a metal. Bisphosphine, bisphosphite, and bis(phosphorus) ligands in general, contain two phosphorus donor atoms and normally form cyclic chelate structures with transition metals.

There is a wealth of information in the art regarding the preparation of phosphorus-containing ligands, their coordination to various metal centers and the properties of the resulting compounds. Many of these ligands are of use the compounds of the present invention.

Other exemplary art-recognized phosphorus-containing ligands of use in the present invention include substituted and unsubstituted bis(8-quinolyl)(3,5-di-tert-butylphenoxy)phosphine, (R)-(−)-1-[(S)-2-diphenylphosphino)ferrocenyl]ethyldi-tert-butylphosphine; [(4R)-[4,4'-bi-1,3-benzodioxole]-5,5'-diyl]bis[bis[3,5-bis(1,1-dimethylethyl)-4-methoxyphenyl]-phosphine; and (R)-(−)-1-(6,6-dimethoxybiphenyl-2,2'-diyl)bis(3,5-dimethylphenyl) phosphine); and combinations thereof. Specific examples of the chiral ligand include cyclohexylanisylmethylphosphine (CAMP), 1,2-bis(anisylphenylphosphino)ethane (DI-PAMP), 1,2-bis(alkylmethylphosphino)ethane (BisP*), 2,3-bis(diphenylphosphino)butane (CHIRAPHOS), 1,2-bis(diphenylphosphino)propane (PROPHOS), 2,3-bis(diphenylphosphino)-5-norbornene (NORPHOS), 2,3-O-isopropylidene-2,3-dihydroxy-1,4-bis(diphenylphosphino) butane (DIOP), 1-cyclohexyl-1,2-bis(diphenylphosphino)ethane (CYCPHOS), 1-substituted-3,4-bis(diphenylphosphino)pyrrolidine (DEGPHOS), 2,4-bis(diphenylphosphino)pentane (SKEWPHOS), 1,2-bis (substituted phospholano)benzene (DuPHOS), 1,2-bis (substituted phospholano)ethane (BPE), 1-(substituted phospholano)-2-(diphenylphosphino)benzene (UCAP-Ph), 1-[bis(3,5-dimethylphenyl)phosphino]-2-(substituted phospholano)benzene (UCAP-DM), 1-(substituted phospholano)-2-[bis(3,5-di(t-butyl)-4-methoxyphenyl)phosphinoThenzene (UCAP-DTBM), 1-(substituted phospholano)-2-(di-naphthalen-1-yl-phosphino)benzene (UCAP-(1-Nap)), 1-[1',2-bis(diphenylphosphino)ferrocenyl]ethylamine (BP-PFA), 1-[1',2-bis(diphenylphosphino)ferrocenyl]ethyl alcohol (BPPFOH), 2,2'-bis(diphenylphosphino)-1,1'-dicyclopentane (BICP), 2,2'-bis(diphenylphosphino)-1,1'-binaphthyl (BINAP), 2,2'-bis(diphenylphosphino)-1,1'-(5,5',6,6',7,7',8,8'-octahydrobinaphthyl)($H_8$-BINAP), 2,2'-bis(di-p-tolylphosphino)-1,1'-binaphthyl (TOL-BINAP), 2,2'-bis [di(3,5-dimethylphenyl)phosphino]-1,1'-binaphthyl (DM-BINAP), 2,2'-bis(diphenylphosphino)-6,6'-dimethyl-1-1'-biphenyl (BICHEP), [4,4'-bi-1,3-benzodioxole]-5,5'-diy]bis [diphenylphosphine] (SEGPHOS), [4,4'-bi-1,3-benzodioxole]-5,5'-diylbis[bis(3,5,-dimethylphenyl) phosphine] (DM-SEGPHOS), [(4S)-[4,4'-bi-1,3-benzodioxole]-5,5'-diyl]bis[bis[3,5,-bis(1,1-dimethylethyl)-4-methoxyphenyl]phosphine] (DTBM-SEGPHOS), etc.

In various embodiments, a ligand in a compound of the invention is a phosphine, phosphinite, phosphonite or phosphite ligand. This ligand is bound to the first row metal center. Similar to phosphine ligands, phosphinite, phosphonite and phosphites have recently emerged as versatile ligands in transition metal catalyzed reactions. Positioning of adjacent electronegative heteroatoms such as N and O (but not limited thereto) allow subtle modulation of electronic properties of these ligands that are often beneficial to catalytic reactions. The presence of adjacent O and N provides additional oxidative stabilities to these ligands compared to their phosphine analogues. These ligands are easy to make in high yield due to availability of large natural and synthetic chiral pool derived amino alcohols and chiral diols (for a modular approach, see Velder, J.; Robert, T.; Weidner, I.; Neudorfl, J.-M.; Lex, J.; Schmalz, H-G. *Adv. Synth. Catal.* 2008, 350, 1309-1315; for a review on synthesis of phosphites, see Montserrat Diéguez, Oscar Pámies, Aurora Ruiz, and Carmen Claver, *Methodologies in Asymmetric Catalysis*, Chapter 11, 2004, pp 161-173 *ACS Symposium Series*, Volume 880 for synthesis of phosphites. See Adriaan J. Minnaard, Ben L. Feringa, Laurent Lefort and Johannes G. de Vries *Acc. Chem. Res.,* 2007, 40 (12), pp 1267-1277 for the synthesis of phosphoramidites).

Examples where phosphinite ligands have been used as ligands for metal-based catalysts include Blankenstein, J.; Pflatz, A. *Angew Chem. Int. Ed.,* 2001, 40, 4445-47) and Pd catalyzed Suzuki cross coupling reaction (Punji, B.; Mague, J. T.; Balakrishna, M. S. *Dalton Trans.,* 2006, 1322-1330), Braunstein, P.; Naud, F.; Pflatz, A.; Rettig, S. *Organometallics,* 2000, 19, 2676-2683), Martorell, A.; Naasz, R.; Ferringa, B. L.; Pringle, P. G. *Tetrahedron Asymmetry,* 2001, 12, 2497-2499 and Peng, X.; Wang, Z.; Xia, C.; Ding, K. *Tetrahedron Lett.,* 2008, 49, 4862-4864).

Rajanbabu and coworkers have prepared nickel compounds supported on phosphinite, phosphite and phosphoramidite ligands and have used these catalysts for asymmetric hydrovinylation reactions (Park, H.; Kumareswaran, R.; Rajanbabu, T. V. R. *Tetrahedron,* 2005, 61, 6352-67). Sandoval et al., have used Rh(I) diphosphite ligands for asymmetric hydrogenation of dehydroamino acid derivatives (Sandoval, C. A.; Liu, S. *J. Molecular. Catalysis. A,* 2010, 325, 65-72). Pd phosphite catalyzed dehalogenation of arenes was reported by Lee et al., (Moon, J.; Lee, S. *J. Organometal. Chem.,* 2009, 694, 473-77). Pd-triphenyl phosphite was shown to catalyze dehydrative allylation using allyl alcohol (Kayaki, Y.; Koda, T.; Ikariya, T. *J. Org. Chem.,* 2004, 69, 2595-97). Pd-based biaryl phosphite catalyst is known to be effective in asymmetric allylic substitution reactions of allyl acetate, carbonate and halides (Dieguez, M.; Pamies, O. *Acc. Chem. Res.,* 2010, 43, 312-22). Calixarene phosphites have been used as hemispherical chelator ligands for obtaining high linear to branched ratio of olefin in Rh(0) catalyzed hydroformylation reaction (Monnereau, L.; Semeril, D.; Matt, D.; Toupet, L. *Adv. Synth. Catal.* 2009, 351, 1629-36).

In various embodiments, the ligand in the compound of the invention is a phosphoramidite ligand. Phosphoramidite ligands have been used in catalytic asymmetric hydrogenations (Minnaard, A. J.; Feringa, B. L.; Lefort, L.; de Vries, J. G. *Acc. Chem. Res.,* 2007, 40, 1267-77), conjugate addition to enones (Jagt, R. B. C.; de Vries, J. G.; Ferringa, B. L.; Minnaard, A. *J. Org. Lett.,* 2005, 7, 2433-35), and allylic alkylation with diethyl zinc (Malda, H.; van Zijl, A. W.; Arnold, L. A.; Feringa, B. L. *Org. Lett.,* 2001, 3, 1169-1171).

b. Synthesis (i) Ligands

In general, the ligands of use in the compounds of the invention, and the compounds themselves, are prepared by art-recognized reactions. A number of exemplary synthetic routes are set forth herein for the purposes of illustration, however, the scope of this illustration is not intended to be limiting.

The ligands are assembles through covalent bonds by reacting precursors for each region of the ligand having reactive functional groups to form a linkage fragment, which is a covalent bond.

Currently favored classes of reactions for use in assembling the compounds of the invention are those proceeding under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups include, for example:

(a) carboxyl groups and derivatives thereof including, but not limited to activated esters, e.g., N-hydroxysuccinimide esters, N-hydroxybenztriazole esters, acid halides, acyl imidazoles, thioesters, p-nitrophenyl esters, alkyl, alkenyl, alkynyl and aromatic esters, activating groups used in peptide synthesis and acid halides;

(b) hydroxyl groups, which can be converted to esters, sulfonates, phosphoramidates, ethers, aldehydes, etc.

(c) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups, which are capable of participating in Diels-Alder reactions such as, for example, maleimido groups;

(e) aldehyde or ketone groups, allowing derivatization via formation of carbonyl derivatives, e.g., imines, hydrazones, semicarbazones or oximes, or via such mechanisms as Grignard addition or alkyllithium addition;

(f) sulfonyl halide groups for reaction with amines, for example, to form sulfonamides;

(g) thiol groups, which can be converted to disulfides or reacted with acyl halides, for example;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds; and (k) phosphoramidites and other standard functional groups useful in nucleic acid synthesis.

The reactive functional groups can be chosen such that they do not participate in, or interfere with, the reactions necessary to assemble or utilize the ligand. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

Certain compounds of the present invention possess asymmetric carbon atoms (optical centers) or double bonds; the racemates, diastereomers, geometric isomers and individual isomers are encompassed within the scope of the present invention. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the disclosure encompasses both E and Z geometric isomers. Likewise, all tautomeric forms are also intended to be included.

In an exemplary embodiment, a ligand of use in the compounds of the invention is prepared according to Scheme I:

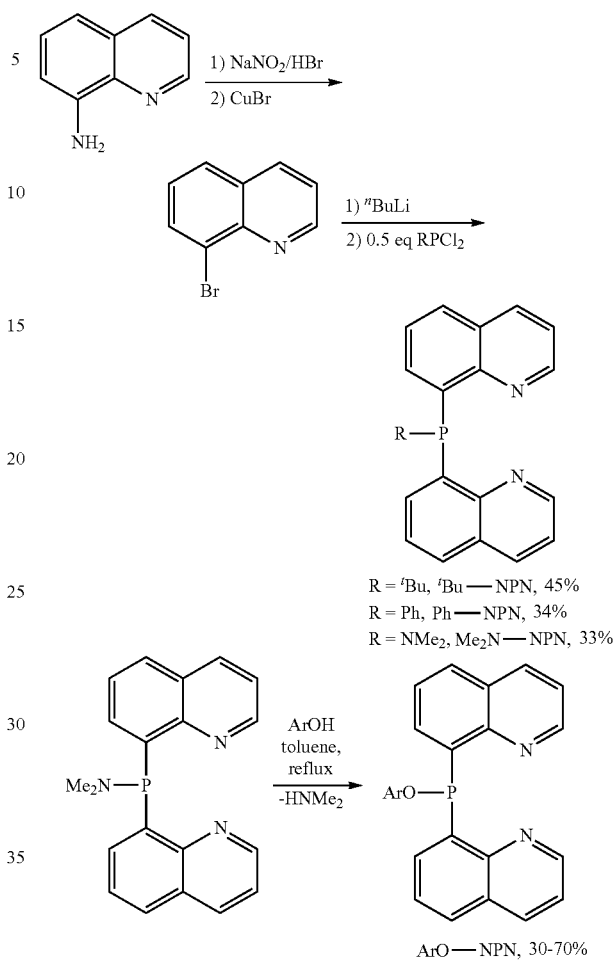

(ii) The Compounds

Compounds of the invention are readily prepared from the ligands by formation of a metal complex with a first row metal according to art-recognized procedures. In various embodiments, the complex is a precursor to a catalytically active compound of the invention. The precursor is converted to the catalytically active compound by abstraction of a ligand from the metal center, resulting in the formation of a cationic first row metal compound of the invention. An exemplary route to the precursor compound and the catalytically active compound is set forth in Scheme II.

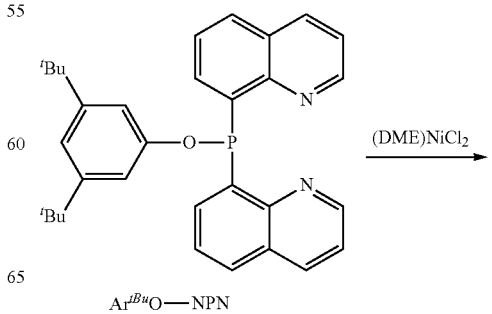

-continued

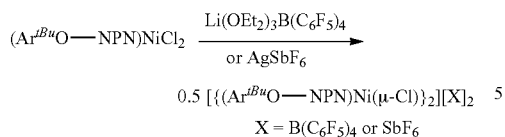

0.5 [{(Ar$^{tBu}$O—NPN)Ni(μ-Cl)}$_2$][X]$_2$

X = B(C$_6$F$_5$)$_4$ or SbF$_6$

As appreciated by those of skill in the art, the conditions set forth in Scheme II can be varied without divergence from the spirit of the present invention and such variations are within the scope of the invention and the claims appended hereto.

c. Hydrosilylation

The compounds of the invention, in an exemplary embodiment, are active catalysts for the addition of the elements of a hydrosilane across a pi-bonded system. Thus, in various embodiments, the invention provides a method of hydrosilylating a pi-bonded species. The method includes contacting the pi-bonded species with a compound of the invention and a hydrosilane under conditions appropriate for hydrosilylating the pi-bonded system. In general terms, the invention provides the method of silylating a pi-bonded species such as that set forth in Scheme III:

Scheme III

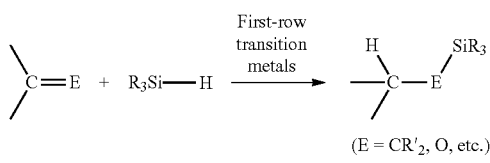

(E = CR'$_2$, O, etc.)

In various embodiments, the catalyst metal loading is modest, yet still produces the desired compounds in excellent yields. Exemplary catalyst loadings are from about 0.05 to about 10 mol %, for example, from about 0.1 mol % to about 5.0 mol %, for example from about 0.5 mol % to about 2.5 mol %.

In an exemplary embodiment, the pi-bonded species is an alkene, and the method of the invention adds the elements of a hydrosilane across the C═C bond as set forth in the various reactions of Scheme IV:

Scheme IV

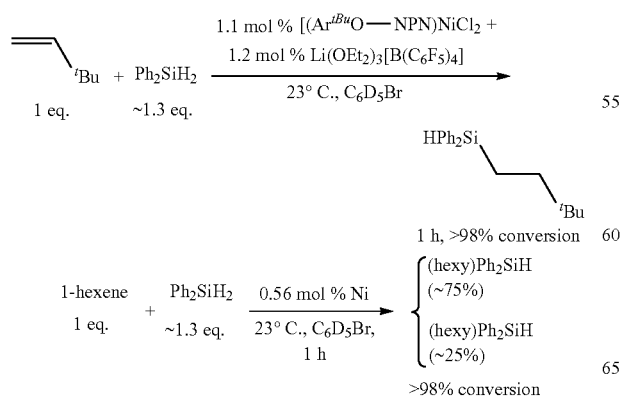

-continued

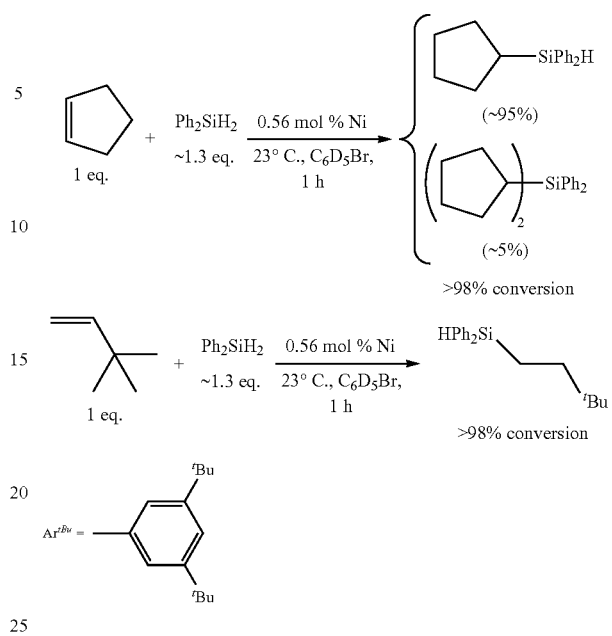

In various embodiments, the invention provides a method of performing silylation of a pi-bonded system with a primary hydrosilane. Examples of such silylations are set forth in Scheme V:

Scheme V

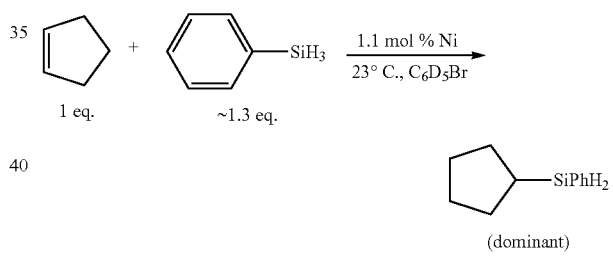

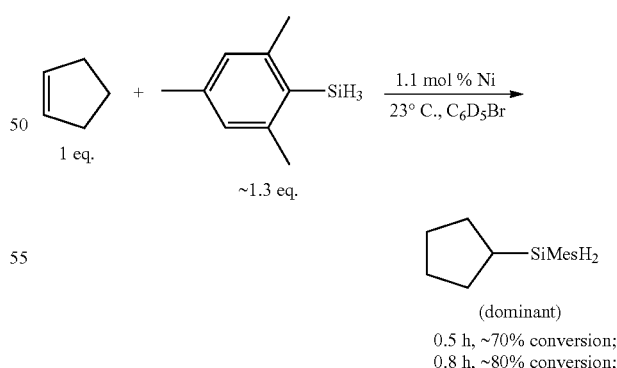

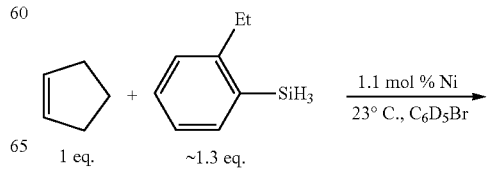

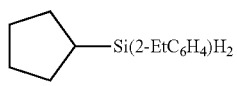

(dominant)

2 h, ~36% conversion;
21 h, ~73% conversion.

In an exemplary embodiment, the invention provides a method of silylating a pi-bonded system with a tertiary hydrosilanes, such as that set forth in Scheme VI:

Scheme VI

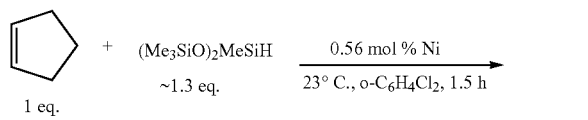

>98% conversion

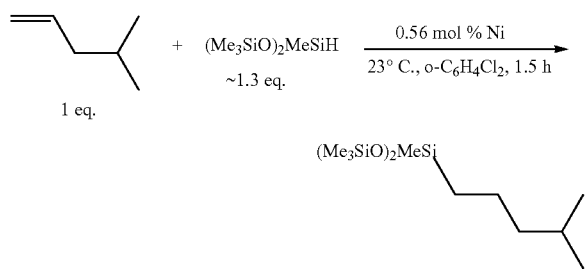

(major product)
>98% conversion

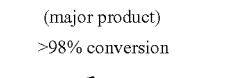

>98% conversion

In various embodiments, the invention provides a method of silylating a pi-bonded system with a reagent other than a hydrosilane. For example, the invention provides a method of hydrosilylating a pi-bonded system with a halohydrosilane as set forth in Scheme VII:

Scheme VII

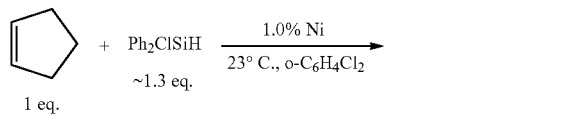

{ 20 h, 34%
48 h, 61%
10 d, 94% }

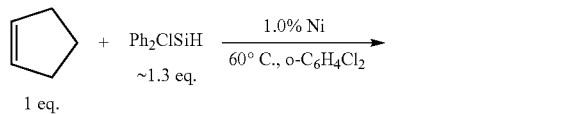

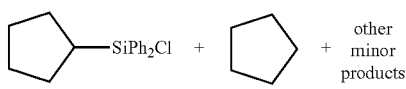

5:1
16.5 h, >93% conversion;

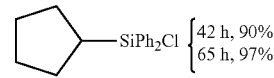

{ 42 h, 90%
65 h, 97% }

The hydrosilyation reactions of the invention can be performed in the presence of a solvent, e.g., preferred solvents are arylchlorides but this could change as more are explored or they can be performed in the absence of a colvent cosolvent as set forth in Scheme VIII:

Scheme VIII

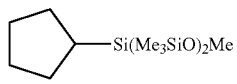

Dominant products
{ (hexyl)Ph$_2$SiH (~88%)
(hexyl)$_2$Ph$_2$Si (~12%) }

2.8 h, > 98% conversion
(~400 turnovers)

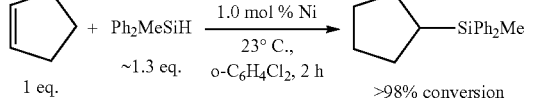

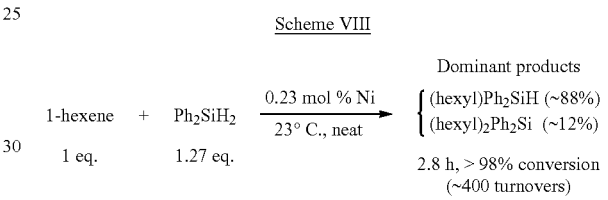

21 h, ~50% conversion
(~200 turnovers)

The hydrosilylation reactions of the invention are performed under ambient or an inert atmosphere. In an exemplary embodiment, the invention provides a hydrosilylation reaction as set forth herein in which the yield of the desired product is higher when the reaction is run under ambient conditions than when it is run otherwise identically but under an inert atmosphere. An example of such an "air effect" in an exemplary reaction of the invention is set forth in Scheme IX:

Scheme IX

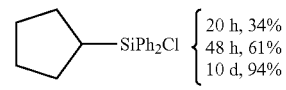

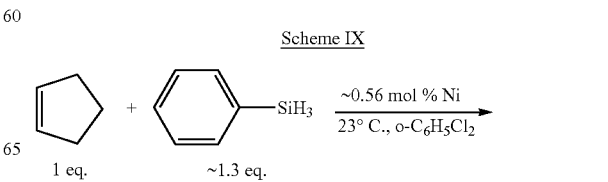

-continued

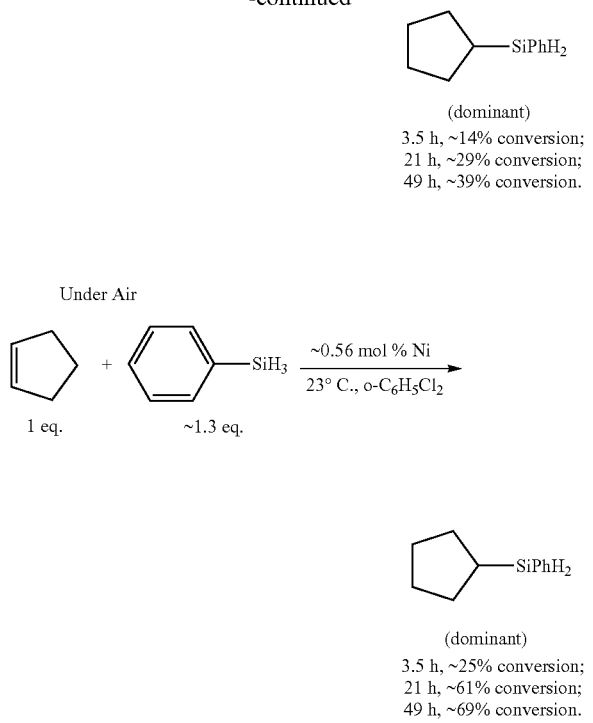

(dominant)
3.5 h, ~14% conversion;
21 h, ~29% conversion;
49 h, ~39% conversion.

Under Air

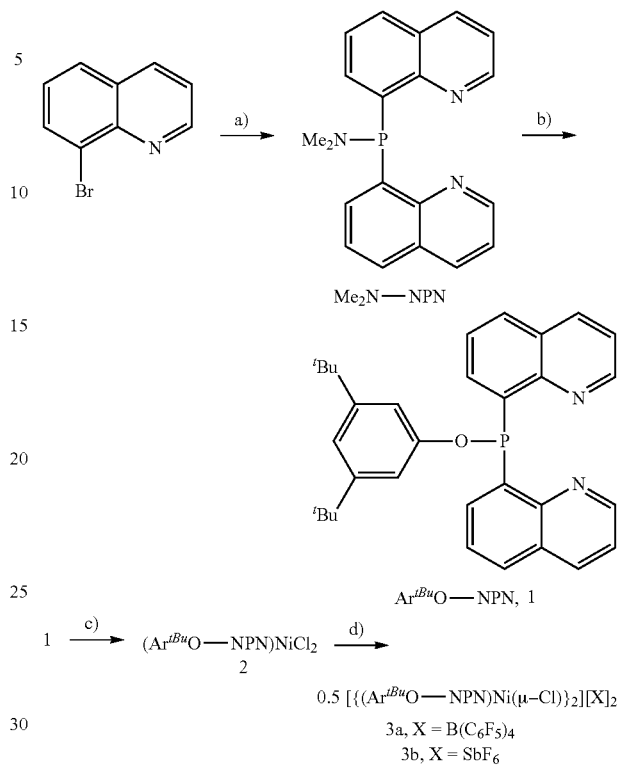

Scheme 1. Synthesis of NPN ligand and Ni complexes

Conditions: a) i) $^n$BuLi; ii) 0.5 equiv. (NMe$_2$)PCl$_2$; b) 3,5-di-tert-butylphenol, toluene, 125° C.; c) Ni(DME)Cl$_2$, CH$_2$Cl$_2$; d) X = B(C$_6$F$_5$)$_4$, Li(OEt$_2$)$_3$B(C$_6$F$_5$)$_4$; X = SbF$_6$, AgSbF$_6$.

The following examples are provided to illustrate selected embodiments of the invention and should not be construed as limiting the scope of the invention or its embodiments.

EXAMPLES

Example 1

General Considerations

All manipulations were carried out using Schlenk techniques under a purified N$_2$ atmosphere or in a Vacuum Atmospheres drybox. Solvents were distilled under N$_2$ from appropriate drying agents and stored in Straus flasks. Benzene-d$_6$ was dried by vacuum distillation from Na/K alloy. Silanes, olefin substrates, 1,2-dichlorobenzene and bromobenzene-d$_5$ were dried over 4 Å molecular sieves or CaH$_2$, and stored under N$_2$. Dichloromethane-d$_2$ was dried with CaH$_2$ and vacuum transferred into a sealed flask. All other reagents were purchased from Aldrich, Strem, or Gelest, and used as received. 8-bromoquinoline[1] was prepared according to literature procedures. NMR spectra were recorded on Bruker AV-600, DRX-500, AV-500, AVB-400, AVQ-400 and AV-300 spectrometers at room temperature. $^1$H NMR spectra were referenced to residual protio solvent peaks (δ 7.16 for C$_6$D$_6$, δ 5.32 for CD$_2$Cl$_2$, δ 7.03 (4-H) for C$_6$D$_5$Br, δ 7.4 (3-H) for o-C$_6$H$_4$Cl$_2$). $^{13}$C{$^1$H} NMR spectra were referenced to solvent resonance (δ 128.4 for C$_6$D$_6$, δ 54.0 for CD$_2$Cl$_2$, δ 122.5 (ipso C) for C$_6$D$_5$Br, δ 127.68 (4-C) for o-C$_6$H$_4$Cl$_2$). $^{31}$P{$^1$H} NMR chemical shifts were referenced to an external H$_3$PO$_4$ standard. Elemental analyses were carried out by the College of Chemistry Microanalytical Laboratory at the University of California, Berkeley. GC-MS analysis was performed on an Agilent Technologies 6890N GC system with an HP-5MS column.

Synthesis of Bis(8-quinolyl)(dimethylamino)phosphine (NMe$_2$-NPN)

N-butyllithium (1.6 M in hexanes, 4 mL, 6.4 mmol) was added dropwise to a stirred solution of 8-bromoquinoline (1.23 g, 5.92 mmol) in THF (40 mL) at –78° C. The mixture was stirred for 15 min at this temperature before Me$_2$NPCl$_2$ (neat, 0.33 mL, 420 mg, 2.88 mmol) was added via syringe. The reaction mixture was stirred for another 10 min at –78° C. before it was allowed to warm to room temperature; stirring was continued for 18 h. All of the volatile material was removed in vacuo and toluene (35 mL) was added. The yellow slurry was stirred at room temperature for 20 min and then filtered. The yellow extract was concentrated to about 20 mL and filtered. The filtrate was further concentrated to about 10 mL and stored at –35° C. for 2 d. The product was obtained as a pale yellow solid in 35% yield (330 mg, 1.0 mmol) and exhibited >95% purity by NMR. It was used without further purification. $^1$H NMR (C$_6$D$_6$, 600.13 MHz): δ 8.62 (m, 2H), 7.54 (m, 2H), 7.39 (m, 2H), 7.17 (m, 2H), 6.72 (m, 2H), 2.86 (d, J=9 Hz). $^{13}$C {$^1$H} NMR (CD$_2$Cl$_2$, 150.92 MHz): δ 150.20 (d, J=18 Hz), 149.81, 140.96 (d, J=17 Hz), 136.65, 133.58, 128.58, 128.45, 126.88, 121.60, 43.71 (d, J=17 Hz). $^{31}$P {$^1$H} NMR (C$_6$D$_6$, 242.95 MHz): δ 54.5. GC-MS m/z 331 (M$^+$), 288, 159. Anal. Calcd. (%) for C$_{20}$H$_{18}$N$_3$P (331.35): C, 72.49; H, 5.47; N, 12.68. Found: C, 72.25; H, 5.55; N, 12.19.

Synthesis of Bis(8-quinolyl)(3,5-di-tert-butylphenoxy)phosphine (Ar$^{tBu}$O-NPN, 1)

A mixture of 1 (600 mg, 1.81 mmol) and 3,5-di-tert-butylphenol (370 mg, 1.79 mmol) in toluene (15 mL) was refluxed under N$_2$ for 6 h (bath temperature was 125° C.). All volatile materials were removed in vacuo. Benzene (8 mL) and hexanes (4 mL) were added and the mixture was filtered through Celite® and a glass fiber filter to give a yellow solution. The volatile components were removed in vacuo. The residue was washed with cold hexanes and dried in vacuo to give the product as a light yellow solid (680 mg, 1.38 mmol, 77%). $^1$H NMR (C$_6$D$_6$, 499.92 MHz): δ 8.59 (m, 2H), 8.06 (m, 2H), 7.71 (m, 2H), 7.46 (m, 2H), 7.36 (m, 2H), 7.28 (m, 1H), 7.13 (m, 2H), 6.66 (m, 2H), 1.30 (s, 18H). $^{13}$C{$^1$H} NMR (CD$_2$Cl$_2$, 150.92 MHz): δ 158.50 (d, J=12 Hz), 152.73, 150.23 (d, J=1.5 Hz), 149.88 (d, J=20 Hz), 141.31 (d, J=23 Hz), 136.70 (d, J=1.5 Hz), 132.97 (d, J=1.5 Hz), 129.94, 128.59, 127.18, 121.96, 116.77, 114.13 (d, J=11 Hz), 35.45, 31.79. $^{31}$P {$^1$H} NMR (C$_6$D$_6$, 242.95 MHz): δ 98.0. Anal. Calcd. (%) for C$_{32}$H$_{33}$N$_2$OP (492.59): C, 78.02; H, 6.75; N, 5.69. Found: C, 77.68; H, 6.69; N, 5.52.

Synthesis of (Ar$^{tBu}$O-NPN)NiCl$_2$ (2)

A solution of 1 (500 mg, 1.02 mmol) in CH$_2$Cl$_2$ (4 mL) was added to a stirring slurry of NiCl$_2$(DME) (200 mg, 0.91 mmol) in CH$_2$Cl$_2$ (10 mL). The reaction mixture was allowed to stir at room temperature for 1 d. All volatile materials were removed in vacuo. The residue was washed with diethyl ether (2 mL×3) and hexanes (8 mL×2), and dried in vacuo to give the product as a light brown solid (340 mg, 0.55 mmol, 60%). The $^1$H NMR spectrum of 2 was not obtained due to the poor solubility of 2 in a range of organic solvents, including dichloromethane. Anal. Calcd. (%) for C$_{32}$H$_{33}$N$_2$OPNiCl$_2$ (622.19): C, 61.77; H, 5.35; N, 4.50. Found: C, 61.80; H, 5.43; N, 4.48.

Synthesis of [{(Ar$^{tBu}$O-NPN)Ni(μ-Cl)}$_2$][B(C$_6$F$_5$)$_4$]$_2$ (3a)

(A) Synthesis and Isolation of 3a from 2 and Li(OEt$_2$)$_3$B(C$_6$F$_5$)$_4$ A solution of Li(OEt$_2$)$_3$B(C$_6$F$_5$)$_4$[2] (180 mg, 0.198 mmol) in C$_6$H$_5$F (4 mL) was added dropwise to a stirring slurry of 2 (114 mg, 0.183 mmol) in C$_6$H$_5$F (6 mL). The resulting solution was stirred at room temperature for 1 d. The reaction mixture was then filtered through Celite® and a glass fiber filter, and layered with hexanes (10 mL). At room temperature a dark oil settled out. The oil was separated from the solution, washed with hexanes (3 ml×4), and dried in vacuo to give the product as a light green solid (220 mg, 0.087 mmol, 95%). $^1$H NMR (C$_6$D$_5$Br, 600.13 MHz): δ 51.7 (2H), 21.3 (2H), 18.6 (4H), 12.9 (2H), 9.6 (3H), 8.1 (2H) (aryl hydrogens, total 15H), 1.0 (18H, $^t$Bu). Anal. Calcd. (%) for C$_{112}$H$_{66}$N$_4$O$_2$P$_2$Ni$_2$Cl$_2$B$_2$F$_{40}$ (2531.54): C, 53.14; H, 2.63; N, 2.21. Found: C, 53.34; H, 3.02; N, 1.92.

(B) In situ generation of 3a from 3b and Li(OEt$_2$)$_3$B(C$_6$F$_5$)$_4$

Bromobenzene-d$_5$ (0.92 g, 0.6 mL) was added to a solid mixture of 3b (3.4 mg, 0.0021 mmol, 1 equiv) and Li(OEt$_2$)$_3$B(C$_6$F$_5$)$_4$ (4.0 mg, 0.0044 mmol, 2.1 equiv). The resulting solution was transferred to a J. Young NMR tube. $^1$H NMR measurements taken after 1.3 h showed quantitative formation of 3a.

Synthesis of [(Ar$^{tBu}$O-NPN)Ni(μ-Cl)(SbF$_6$)]$_2$ (3b)

A mixture of 2 (41 mg, 0.066 mmol) and AgSbF$_6$ (24 mg, 0.070 mmol) in CH$_2$Cl$_2$ (4 mL) was stirred at room temperature for 1.5 h. The reaction mixture was filtered through Celite® and a glass fiber filter, and pentane (6 mL) was added to precipitate a light green solid. The solid was washed with pentane (4 mL×2), and dried in vacuo to give 3b as a light green powder (43 mg, 0.026 mmol, 79%). $^1$H NMR (C$_6$D$_5$Br, 500.23 MHz): δ 50.2 (2H), 22.4 (2H), 19.2 (2H), 18.0 (2H), 13.1 (2H), 9.0 (3H), 8.1 (2H) (aryl hydrogens, total 15H), 1.0 (18H, $^t$Bu). Anal. Calcd. (%) for C$_{64}$H$_{66}$N$_4$O$_2$P$_2$Ni$_2$Cl$_2$Sb$_2$F$_{12}$ (1644.97): C, 46.73; H, 4.04; N, 3.41. Found: C, 46.39; H, 4.16; N, 3.35. Crystals suitable for X-ray analysis were grown from vapor diffusion of hexanes into a C$_6$H$_5$F solution of 3b at room temperature.

In situ Generation of [(Ar$^{tBu}$O-NPN)$_2$Ni$_2$(μ-Cl)$_3$][B(C$_6$F$_5$)$_4$] (4a)

A solution of Li(OEt$_2$)$_3$B(C$_6$F$_5$)$_4$ (8.3 ing, 0.0044 mmol, 0.5 equiv) in bromobenzene-d$_5$ (1.2 g, ca. 0.8 mL) was added to 2 (5.5 mg, 0.0088 mmol, 1.0 equiv) in a J. Young NMR tube. The contents were well shaken and the reaction mixture was allowed to stand at room temperature. $^1$H NMR measurements taken after 1 h show quantitative formation of a new paramagnetic species with NMR data very similar to that of 4b, which we assume to be [(Ar$^{tBu}$O-NPN)$_2$Ni$_2$(μ-Cl)$_3$][B(C$_6$F$_5$)$_4$] (4a). NMR (C$_6$D$_5$Br, 500.23 MHz): δ 44.9, 19.9, 17.5, 16.2, 11.6, 7.9 (aryl hydrogens, total 15H), 1.3 (18H, $^t$Bu).

Synthesis of [(Ar$^{tBu}$O-NPN)$_2$Ni$_2$(μ-Cl)$_3$][SbF$_6$](4b)

A mixture of 2 (40 mg, 0.064 mmol) and LiSbF$_6$ (16 mg, 0.066 mmol) in fluorobenzene (4 mL) was stirred at room temperature for 2 d. All volatiles were removed in vacuo. CH$_2$Cl$_2$ (2 mL) was added, and the resulting orange solution was filtered through Celite® and a glass fiber filter, and concentrated to ca. 1 mL. Hexanes (3 mL) were added to precipitate a light orange/brown solid. The solid was washed with hexanes (2 mL×3), and dried in vacuo to give 4b as a light orange/brown powder (32 mg, 0.022 mmol, 69%). $^1$H NMR (CD$_2$Cl$_2$, 500.23 MHz): δ 45.5, 20.7, 18.2, 16.9, 11.1, 7.6, 7.4 (aryl hydrogens, total 15H), 1.2 (18H, $^t$Bu). $^1$H NMR (C$_6$D$_5$Br, 500.23 MHz): δ 45.2, 20.0, 17.7, 16.4, 11.8, 8.0 (aryl hydrogens, total 15H), 1.2 (18H, $^t$Bu). Anal. Calcd. (%) for C$_{64}$H$_{66}$N$_4$O$_2$P$_2$Ni$_2$Cl$_3$SbF$_6$ (1444.68): C, 53.21; H, 4.60; N, 3.88. Found: C, 52.80; H, 4.83; N, 3.77. Crystals suitable for X-ray analysis were grown from vapor diffusion of hexanes into a CH$_2$Cl$_2$ solution of 4b at room temperature. Crystals of 4b were grown from layering hexanes onto a solution of 4b in CH$_2$Cl$_2$ at 23° C. X-ray crystallography indicated a three chloride-bridged structure for the {[(Ar$^{tBu}$O-NPN)Ni]$_2$(μ-Cl)$_3$}$^+$ cation (Figure S1), although the data is not of sufficient quality to establish the accurate bond angles and distances.

Results

The new ligand 1 was obtained via bis(8-quinolyl)(dimethylamino)phosphine in moderate yield by lithiation of 8-bromoquinoline followed by addition of 0.5 equivs of (NMe$_2$)PCl$_2$. Treatment of this synthetic intermediate with 3,5-di-tert-butylphenol in refluxing toluene provided Ar$^{tBu}$O-NPN (1) in 77% yield. Reaction of 1 with Ni(DME)Cl$_2$ (DME=dimethoxyethane) in dichloromethane afforded an insoluble product characterized as the dichloride (Ar$^{tBu}$O-NPN)NiCl$_2$ (2) (Scheme 1). Abstraction of chloride from 2 with 1.1 equiv of Li(OEt$_2$)$_3$B(C$_6$F$_5$)$_4$ in bromobenzene-d$_5$ generated the corresponding, solvated cationic nickel monochloride complex in situ. The addition of tert-butylethylene (90 equiv) and Ph$_2$SiH$_2$ (114 equiv) to this solution cleanly yielded the hydrosilylation product Ph$_2$SiHCH$_2$CH$_2$$^t$Bu within 1 h at 23° C.

This finding motivated a more detailed study of (Ar$^{tBu}$O-NPN)Ni cationic complexes as hydrosilylation catalysts, and attempts to isolate the nickel monochloride complexes [(Ar$^{tBu}$O-NPN)NiCl]X (X=B(C$_6$F$_5$)$_4$, 3a; X=SbF$_6$, 3b) via treatment of 2 with a slight excess of Li(OEt$_2$)$_3$B(C$_6$F$_5$)$_4$ or AgSbF$_6$ (Scheme 1). 3a can also be generated in situ via treatment of 3b with 2.1 equiv. of Li(OEt$_2$)$_3$B(C$_6$F$_5$)$_4$. See supporting information for details. While multiple attempts to obtain X-ray quality crystals of 3a inevitably produced oily material, the crystal structure of 3b was readily obtained. Thus, 3b was found to adopt a dimeric, dicationic structure in the solid state (FIG. 1). A rather unusual structural feature of 3b is coordination of the "weakly coordinating" SbF$_6$ anion, characterized by a short Ni—F distance of 2.262(4) Å. The Sb—F distance associated with this interaction is 1.904(4) Å, about 0.032 Å longer than the average terminal Sb—F bond. Very rare examples of coordination of the SbF$_6$$^-$ anion to a transition metal center: (a) Hersh, W. H. *J. Am. Chem. Soc.* 1985, 107, 4599. (b) Brochler, R.; Sham, I. H. T.; Bodenbinder, M. Schmitz, V. Rettig, S. J.; Trotter, J. Willner, H.; Aubke, F. *Inorg. Chem.* 2000, 39, 2172.

Complexes 3a,b were investigated as precatalysts for the hydrosilylation of alkenes. While 3b shows modest activities for hydrosilylations of cyclopentene with Ph$_2$SiH$_2$ (ca. 26% conversion after 18 h at 23° C. with 0.56 mol % Ni loading), its [B(C$_6$F$_5$)$_4$] anion analog 3a is much more effective and results in complete conversion within 1 h (Table 1, entries 1 and 2). Secondary hydrosilanes are the most efficient substrates for hydrosilylations catalyzed by 3a. Reactions were generally carried out in bromobenzene-d$_5$ (entries 1-11), but fluorobenzene, chlorobenzene and 1,2-dichlorobenzene are also suitable solvents. Results of typical catalytic runs are listed in Table 1. Conversions were determined by NMR spectroscopies and the identities of the products were further confirmed by GC-MS analysis. With Ph$_2$SiH$_2$ as the reductant, complete hydrosilylation of tert-butylethylene, cyclopentene, 4-methyl-1-pentene, and 1-hexene proceeded to completion at 23° C. within 1 h with 0.56 mol % Ni loading (entries 2-5). The hydrosilylation product distribution appears to depend on the steric properties of the alkene substrates. In general, the mono-hydrosilylation product is dominant but especially with less hindered alkenes, small quantities of the double-hydrosilylation product are produced (entries 2, 4 and 5). Thus the relative reactivities of alkene substrates for double-hydrosilylation follow the trend: 1-hexene>4-methyl-1-pentene>cyclopentene>tert-butylethylene. Note that with the sterically encumbered alkene tert-butylethylene, the mono-hydrosilylation product Ph$_2$SiHCH$_2$CH$_2$$^t$Bu is exclusively formed (entry 3).

Further reduction of the catalyst loading proved possible, as demonstrated by use of 0.1 mol % Ni loading to achieve the hydrosilylation of 1-hexene in 17 h at 23° C. (ca. 1000 turnovers; entry 6). Hydrosilylation reactions may also be carried out in neat 1-hexene and complete reaction occurred within 3 h at 23° C. at a catalyst loading of 0.23 mol % (entry 7). Other secondary hydrosilanes, such as PhMeSiH$_2$ and Et$_2$SiH$_2$, were also effective for this reaction (entries 8 and 9). In contrast to Chirik's neutral bis(imino)pyridine iron system[5], hydrosilylations catalyzed by 3a are generally less efficient for primary (vs. secondary) silanes. Entry 10 shows that hydrosilylation of cyclopentene with PhSiH$_3$ occurred at a 0.92 mol % Ni loading but with only 52% conversion after 47 h at 23° C. Interestingly, under identical reaction conditions hydrosilylation with the bulkier silane MesSiH$_3$ (Mes=2,4,6-C$_6$H$_2$Me$_3$) is much more rapid (entry 11).

TABLE 1

Nickel-Catalyzed Hydrosilylation of Alkenes.$^{a,b}$ $$\diagdown\!\!\diagup_R + R'_3SiH \xrightarrow[23°\ C.]{0.1\text{-}3.0\ \text{mol \% Ni}} R'_3Si\diagdown\!\!\diagup_R$$

| entry | Ni mol % | Olefin | Silane | t h | Conv.$^c$ % |
|---|---|---|---|---|---|
| 1 | 0.56 | cyclopentene | Ph$_2$SiH$_2$ | 18 | 26 |
| 2$^d$ | 0.56 | cyclopentene | Ph$_2$SiH$_2$ | 1 | >98 |
| 3 | 0.56 | $^t$BuCH=CH$_2$ | Ph$_2$SiH$_2$ | 1 | >98 |
| 4$^e$ | 0.56 | 4-methyl-1-pentene | Ph$_2$SiH$_2$ | 1 | >98 |
| 5$^f$ | 0.56 | 1-hexene | Ph$_2$SiH$_2$ | 1 | >98 |
| 6$^f$ | 0.10 | 1-hexene | Ph$_2$SiH$_2$ | 17 | >98 |
| 7$^g$ | 0.23 | 1-hexene | Ph$_2$SiH$_2$ | 3 | >98 |
| 8 | 0.56 | cyclopentene | PhMeSiH$_2$ | 0.5 | 92 |
|   |   |   |   | 28 | >98 |
| 9 | 0.56 | $^t$BuCH=CH$_2$ | Et$_2$SiH$_2$ | 26 | 96 |
| 10$^h$ | 0.56 | 4-methyl-1-pentene | Ph$_2$MeSiH | 1.5 | >98 |
| 11 | 1.0 | cyclopentene | Ph$_2$MeSiH R$_2$MeSiH | 2 | >98 |
| 12 | 0.56 | cyclopentene | (R = Me$_3$SiO) | 1.5 | >98 |
| 13 | 3.0 | cyclopentene | Ph$_2$ClSiH | 42 | 90 |
|   |   |   |   | 65 | 97 |
| 14$^i$ | 0.56 | cyclopentene | PhSiH$_3$ | 20 | 22 |
|   |   |   |   | 41 | 30 |
| 15$^i$ | 0.56 | cyclopentene | MesSiH$_3$ | 1.1 | 75 |

With regards to Table 1:
$^a$Hydrosilylation catalysis were carried out using 3a except entry 1 with 3b.
$^b$General conditions: entries 1-6 and 8-9, silanes (1.27 equiv.), 23° C., C$_6$D$_5$Br; entries 10-11, silanes (1.04 equiv.), 23° C., C$_6$D$_5$Br; entries 12-15, silanes (1.27 equiv.), 23° C., o-C$_6$H$_4$Cl$_2$.
$^c$Conversion was determined by NMR spectroscopy on the basis of the consumption of alkenes and formation of hydrosilylation products, and the identity of the product was confirmed by GC-MS.
$^d$In addition to Ph$_2$SiH(Cyclopentyl), Ph$_2$Si(Cyclopentyl)$_2$ (<5%) was also formed.
$^e$Hydrosilylation product distribution: Ph$_2$SiH(CH$_2$)$_3$CH(CH$_3$)$_2$ and Ph$_2$Si[(CH$_2$)$_3$CH(CH$_3$)$_2$]$_2$ (5.3:1 ratio).
$^f$Hydrosilylation product distribution: Ph$_2$SiH(CH$_2$)$_5$CH$_3$ and Ph$_2$Si[(CH$_2$)$_5$CH$_3$]$_2$ (3:1 ratio).
$^g$The reaction was carried out without a solvent; Hydrosilylation product distribution: Ph$_2$SiH(CH$_2$)$_5$CH$_3$ and Ph$_2$Si[(CH$_2$)$_5$CH$_3$]$_2$ (7.3:1 ratio).
$^h$In addition to expected hydrosilylation product, very small amounts of cyclopentane and other unidentified silicon-containing products were observed.
$^i$Very small amounts of unidentified products in addition to hydrosilylation product were observed.

Attempts to hydrosilylate cyclopentene with tertiary silanes in bromobenzene often led to decomposition of the catalyst and low conversions, presumably due to reaction of active nickel species with aryl bromide. More effective catalysis with tertiary silanes is observed with less reactive solvents, such as 1,2-dichlorobenzene or chlorobenzene (entries 12-15). In the presence of 0.56 mol % catalyst, the hydrosilylation of 4-methyl-1-pentene with Ph$_2$MeSiH proceeded to completion in less than 1.5 h (entry 12). Cyclopentene can also be readily hydrosilylated with Ph$_2$MeSiH at 1.0 mol % Ni loading (entry 13). At a catalyst loading of 0.56 mol %, the complete hydrosilylation of cyclopentene with the commercially relevant silane (Me$_3$SiO)$_2$MeSiH occurred within 1.5 h at 23° C. (entries 14). Hydrosilylation of cyclopentene with Ph$_2$SiClH is slow, requiring 10 d for approximately 94% conversion at 1.0 mol % of Ni loading (entry 15).

The mechanism of this nickel-catalyzed hydrosilylation is currently not well understood, but some observations are potentially relevant. Reaction of paramagnetic complex 3a with $Ph_2SiH_2$ results in rapid formation of $Ph_2SiHCl$ and diamagnetic nickel species which appear to initiate the hydrosilylation reaction. In situ NMR monitoring of the operating catalytic system also revealed the formation of $Ph_2SiHCl$ at early stages of the catalysis. Simple mechanisms that might be considered at this stage involve insertion of the olefin into a Ni—H and/or Ni—Si bond (e.g., involving a hydride species such a $(NPN)NiH^+$), followed by elimination (C—Si or C—H) of the product upon reaction with another equivalent of silane. Selective examples: (a) Speier, J. L.; Webster, J. A.; Barnes, G. H. *J. Am. Chem. Soc.* 1957, 79, 974. (b) Speier, J. L.; Hook, D. E. Dow Corning Corp., U.S. Pat. No. 2,823,218 A 1958. (c) Karstedt, B. D. General Electric Company, U.S. Pat. No. 3,775,452 A 1973. (d) Chalk, A. J.; Harrod, J. F. *J. Am. Chem. Soc.* 1965, 87, 16. (e) Seitz, F.; Wrighton, M. S. *Angew. Chem. Int. Ed. Engl.* 1988, 27, 289. (f) Duckett, S. B.; Perutz, R. N. *Organometallics* 1992, 11, 90. (g) LaPointe, A. M.; Rix, F. C.; Brookhart, M. *J. Am. Chem. Soc.* 1997, 119, 906. (h) Glaser, P. B.; Tilley, T. D. *J. Am. Chem. Soc.* 2003, 125, 13640; Brookhart, M.; Grant, B. E. *J. Am. Chem. Soc.* 1993, 115, 2151. A catalytic reaction with diphenylsilane-d$_2$ and tert-butylethylene with a Ni loading of 1.0 mol % yields an approximately 1:1.6 ratio of $Ph_2SiDCHDCH_2{}^tBu$ and $Ph_2SiDCH_2CHD{}^tBu$ (eq 1). This result implies that rapid, reversible insertion/deinsertion reactions occur before elimination of the hydrosilylation product.[2g,4]

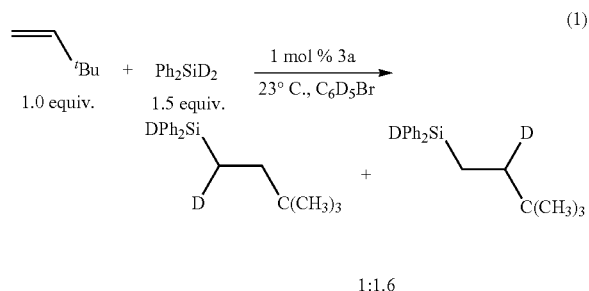

(1)

1:1.6

In summary, a readily accessible and efficient nickel-based catalytic system for the hydrosilylation of alkenes with a broad spectrum of hydrosilanes is described. Work is in progress to fully explore the scope and mechanism of this hydrosilylation reaction. Of particular interest is synthesis and isolation of potential intermediates in this (NPN)Ni catalytic system, and exploration of their stoichiometric and catalytic reactivities. In addition, further improvement of the catalyst activity via ligand modification is currently being investigated.

Example 2

Hydrosilylation of tert-Butylethylene with $Ph_2SiH_2$ using an in situ Generated Catalyst from 3 and $Li(OEt_2)_3B(C_6F_5)_4$ Bromobenzene-d$_5$ (1 g, 0.65 mL) was added to a solid mixture of 2 (5 mg, 0.008 mmol, 1.09 mol %) and $Li(OEt_2)_3B(C_6F_5)_4$ (8.3 mg, 0.0091 mmol, 1.23 mol %). The mixture was shaken to allow mixing. After 5 min the solution was added to a mixture of tert-butylethylene (62 mg, 0.737 mmol, 1.0 equiv) and $Ph_2SiH_2$ (173 mg, 0.939 mmol, 1.27 equiv). The resulting mixture was transferred to a J. Young NMR tube. The reaction went to completion before the first NMR measurement (<0.6 h).

Hydrosilylation of Cyclopentene with $Ph_2SiH_2$ Using 0.28 mol % 3b (0.56 mol % Ni A solution of 3b (3.4 mg, 0.00207 mmol, 0.56 mol % Ni) in $C_6D_5Br$ (0.92 g, 0.6 mL) was added to a mixture of cyclopentene (50 mg, 0.737 mmol, 1.0 equiv) and $Ph_2SiH_2$ (173 mg, 0.939 mmol, 1.27 equiv). The resulting orange solution was transferred to a J. Young NMR tube. The reaction mixture was allowed to stand at room temperature and the reaction progress was monitored by NMR spectroscopy. Hydrosilylation products were identified by $^1H$ and $^{13}C\{^1H\}$ NMR spectroscopies.

General Procedure for the Hydrosilylation of Alkenes Using 0.28 mol % 3a (0.56 mol % Ni)

A solution of 3a (5.3 mg, 0.00209 mmol, 0.56 mol % Ni) in $C_6D_5Br$ (0.92 g, 0.6 mL) (or in o-$C_6H_4Cl_2$ (0.77 g, 0.6 mL)) was added to a mixture of alkene substrate (0.737 mmol, 1.0 equiv) and silane (0.939 mmol, 1.27 equiv). The resulting solution was transferred to a J. Young NMR tube. The reaction mixtures were allowed to stand at room temperature and the reaction progress was monitored by NMR spectroscopy. The hydrosilylation products were identified by $^1H$ and $^{13}C\{^1H\}$ NMR spectroscopies. The reaction mixture was then exposed to air, diluted with hexanes, filtered through a glass fiber filter and analyzed by GC-MS.

General Procedure for the Hydrosilylation of Alkenes Using 0.5 mol % 3a (1.0 mol % Ni)

A solution of 3a (9.4 mg, 0.00371 mmol, 1.0 mol % Ni) in o-$C_6H_4Cl_2$ (0.77 g, 0.6 mL) was added to a mixture of alkene substrate (0.737 mmol, 1.0 equiv) and silane (0.939 mmol, 1.27 equiv). The resulting solution was transferred to a J. Young NMR tube. The reaction mixture was allowed to stand at room temperature and the reaction progress was monitored by NMR spectroscopy. The hydrosilylation products were identified by $^1H$ and $^{13}C\{^1H\}$ NMR spectroscopies. The reaction mixture was then exposed to air, diluted with hexanes, filtered through a glass fiber filter and analyzed by GC-MS.

General Procedure for the Hydrosilylation of Cyclopentene with Primary Hydrosilanes Using 0.28 mol % 3a (0.56 mol % Ni) in o-$C_6H_4Cl_2$ A solution of 3a (5.3 mg, 0.00209 mmol, 0.56 mol % Ni) in o-$C_6H_4Cl_2$ (0.77 g, 0.6 mL) was added to a mixture of cyclopentene (50 mg, 0.737 mmol, 1.0 equiv.) and silane (0.939 mmol, 1.27 equiv). The resulting solution was transferred to a J. Young NMR tube. The reaction mixture was allowed to stand at room temperature and the reaction progress was monitored by NMR spectroscopy. The hydrosilylation products were identified by $^1H$ and $^{13}C\{^1H\}$ NMR spectroscopies. The reaction mixture was then exposed to air, diluted with hexanes, filtered through a glass fiber filter and analyzed by GC-MS.

Hydrosilylation of 1-Hexene with $Ph_2SiH_2$ Using 0.05 mol % 3a (0.1 mol % Ni)

A stock solution of 3a (7 mM, 14 mM Ni) was prepared in $C_6D_5Br$. A solution of 1-hexene (62 mg, 0.737 mmol, 1.0 equiv) and Ph₂SiH₂ (173 mg, 0.939 mmol, 1.27 equiv) in C₆D₅Br (0.92 g, 0.6 mL) was added to an aliquot (50 μL, 0.095 mol % Ni) of this stock solution in a J. Young NMR tube. The reaction mixture was allowed to stand at room temperature and the progress was monitored by NMR spectroscopy. The hydrosilylation products was identified by $^1$H and $^{13}$C{$^1$H} NMR spectroscopy.

Hydrosilylation of 1-Hexene with Ph₂SiH₂ Catalyzed by 3a without Solvent

A mixture of 1-hexene (155 mg, 1.84 mmol, 1.0 equiv) and Ph₂SiH₂ (433 mg, 2.35 mmol, 1.28 equiv) was added to 3a (5.5 mg, 0.00217 mmol, 0.23 mol % Ni) in a J. Young NMR tube with a sealed capillary tube with C₆D₆ for a NMR lock. The reaction mixture was allowed to stand at room temperature and the reaction progress was monitored by NMR spectroscopy. The hydrosilylation products were identified by $^1$H and $^{13}$C NMR spectroscopies.

Hydrosilylation of Cyclopentene with Ph₂ClSiH Using 1.5 mol % 3a (3.0 mol % Ni)

A solution of 3a (28.2 mg, 0.0111 mmol, 3.0 mol % Ni) in o-C₆H₄Cl₂ (0.77 g, 0.6 mL) was added to a mixture of cyclopentene (50 mg, 0.737 mmol, 1.0 equiv) and Ph₂ClSiH (205 mg, 0.939 mmol, 1.27 equiv). The resulting orange solution was transferred to a J. Young NMR tube. The reaction mixture was allowed to stand at room temperature and the reaction progress was monitored by NMR spectroscopy. Hydrosilylation products were identified by $^1$H and $^{13}$C{$^1$H} NMR spectroscopies.

Hydrosilylation of tert-Butylethylene with Ph₂SiD₂ Catalyzed by 3a

A solution of 3a (2.2 mg, 0.00087 mmol, 1.05 mol % Ni) in C₆D₅Br (0.94 g, 0.6 mL) was added to a mixture of tert-butylethylene (14 mg, 0.166 mmol, 1.0 equiv) and Ph₂SiD₂ (47 mg, 0.252 mmol, 1.52 equiv). The resulting solution was transferred to a J. Young NMR tube. The reaction mixture was allowed to stand at room temperature and the reaction progress was followed by $^1$H and $^{13}$C{$^1$H} NMR spectroscopies. Analysis of the NMR spectra by comparison to $^{13}$C{$^1$H} NMR data of undeuterated Ph₂SiHCH₂CH₂$^t$Bu revealed an approximately 1:1.6 ratio of Ph₂SiDCHDCH₂$^t$Bu and Ph₂SiDCH₂CHD$^t$Bu. $^{13}$C NMR (C₆D₅Br, 125.72 MHz): Ph₂SiDCH₂CHD$^t$Bu: δ 38.14 (t, $J_{D,C}$=19 Hz), 6.60 (s); Ph₂SiDCHDCH₂$^t$Bu: δ 38.48 (s), 6.35 (t, $J_{D,C}$=19 Hz).

Characterization of Hydrosilylation Products

Ph₂SiHCH₂CH₂$^t$Bu: $^1$H NMR (C₆D₅Br, 400.13 MHz): δ 5.05 (t, J=3.6 Hz, Si—H, 1H), 1.42-1.38 (m, 2H), 1.15-1.09 (m, 2H), 0.86 (s, 9H). $^{13}$C{$^1$H} NMR (C₆D₅Br, 125.75 MHz): δ 135.38, 134.73, 129.75, 128.26, 38.59, 31.28, 28.96, 6.81. GC-MS m/z 268 (M⁺), 183, 162, 105.

Ph₂SiH(Cyclopentyl): $^1$H NMR (C₆D₅Br, 600.13 MHz): δ 4.96 (Si—H, 1H), 1.92-1.82 (m, 2H), 1.60-1.42 (m, 7H). $^{13}$C{$^1$H} NMR (C₆D₅Br, 125.75 MHz): δ 135.65, 134.71, 129.65, 128.15, 29.44, 27.22, 22.90. GC-MS: Ph₂SiH(Cyclopentyl): m/z 252 (M⁺), 183, 105. Ph₂Si(Cyclopentyl)₂: m/z 320 (M⁺), 251, 183, 105.

Ph₂SiH(CH₂)₃CH(CH₃)₂: NMR (C₆D₅Br, 600.13 MHz): δ 7.60-7.59 (m, overlap with Ph₂Si[(CH₂)₃CH(CH₃)₂]₂), 7.30-7.26 (m, overlap with Ph₂Si[(CH₂)₃CH(CH₃)₂]₂), 5.06 (t, J=3.6 Hz, Si—H, 1H), 1.53-1.46 (m, overlap with Ph₂Si[(CH₂)₃CH(CH₃)₂]₂), 1.28-1.23 (m, overlap with Ph₂Si[(CH₂)₃CH(CH₃)₂]₂), 1.16-1.11 (m, overlap with Ph₂Si[(CH₂)₃CH(CH₃)₂]₂), 0.84 (m, overlap with Ph₂Si[(CH₂)₃CH(CH₃)₂]₂). $^{13}$C{$^1$H} NMR (C₆D₅Br, 150.92 MHz): δ 135.37, 134.81, 129.71, 128.23, 42.73, 27.76, 22.82, 22.50, 12.58. Ph₂Si[(CH₂)₃CH(CH₃)₂]₂: $^{13}$C{$^1$H} NMR (C₆D₅Br, 150.92 MHz): δ 136.84, 135.11, 129.30, 128.05, 43.32, 27.62, 22.86, 21.77, 12.98. GC-MS: Ph₂SiH(CH₂)₃CH(CH₃)₂: m/z 267 ((M-H)), 190, 183, 105. Ph₂Si[(CH₂)₃CH(CH₃)₂]₂: m/z 351 ((M-H)), 337, 274, 267, 183, 105.

Ph₂SiH(CH₂)₅CH₃: $^1$H NMR (C₆D₅Br, 300.13 MHz): δ 7.61-7.58 (m, overlap with Ph₂Si[(CH₂)₅CH₃]₂), 7.31-7.25 (m, overlap with Ph₂Si[(CH₂)₅CH₃]₂), 5.05 (t, J=3.6 Hz, Si—H, 1H), 1.51-1.11 (m, overlap with Ph₂Si[(CH₂)₅CH₃]₂), 0.87 (t, J=7 Hz, overlap with Ph₂Si[(CH₂)₅CH₃]₂). $^{13}$C{$^1$H} NMR (C₆D₅Br, 75.48 MHz): δ 135.38, 134.81, 129.70, 128.22, 33.23, 31.77 (overlap with Ph₂Si[(CH₂)₅CH₃]₂), 24.74, 22.95, 14.50 (overlap with Ph₂Si[(CH₂)₅CH₃]₂), 12.51. Ph₂Si[(CH₂)₅CH₃]₂: $^{13}$C{$^1$H} NMR (C₆D₅Br, 150.92 MHz): δ 136.84, 135.14, 129.29, 128.05, 33.80, 31.77 (overlap with Ph₂SiH(CH₂)₅CH₃), 24.07, 23.02, 14.50 (overlap with Ph₂SiH(CH₂)₅CH₃), 12.92. GC-MS: Ph₂SiH(CH₂)₅CH₃: m/z 268 (M⁺), 183, 105. Ph₂Si[(CH₂)₅CH₃]₂: m/z 352 (M⁺), 267, 183, 105.

Et₂SiHCH₂CH₂$^t$Bu: $^1$H NMR (C₆D₅Br, 400.13 MHz): δ 3.79 (m, Si—H, 1H), 1.24-1.20 (m, 2H), 1.00-0.94 (m, overlap with excess Et₂SiH₂), 0.86 (s, 9H), 0.61-0.50 (m, overlap with excess Et₂SiH₂). $^{13}$C{$^1$H} NMR (C₆D₅Br, 100.62 MHz): δ 38.85, 31.24, 28.99, 8.58, 4.93, 3.03. GC-MS m/z 172 (M⁺), 157, 143, 129, 115.

PhMeSiH(cyclopentyl): $^1$H NMR (C₆D₅Br, 499.92 MHz): δ 7.58-7.50 (m), 7.30-7.25 (m), 4.43 (m, Si—H, overlap with excess PhMeSiH₂), 1.77 (m), 1.56-1.41 (m), 1.35 (m), 1.10 (m), 0.30 (d, J=4 Hz, overlap with excess PhMeSiH₂). $^{13}$C{$^1$H} NMR (C₆D₅Br, 125.72 MHz): δ 136.42, 134.79, 129.37, 128.04, 29.25, 28.89, 27.25, 27.22, 23.94, −6.55. GC-MS m/z 190 (M⁺), 121, 112, 105.

Ph₂MeSi(cyclopentyl): $^1$H NMR (o-C₆H₄Cl₂, 600.13 MHz): δ 7.76-7.74 (m, overlap with excess PhMeSiH₂), 7.50-7.48 (m, overlap with excess PhMeSiH₂), 2.02 (m, 2H), 1.73-1.57 (m, 7H), 0.72 (s, 3H). $^{13}$C{$^1$H} NMR (o-C₆H₄Cl₂, 150.92 MHz): δ 137.31, 134.89 (overlap with excess Ph₂MeSiH), 129.12, 127.86, 28.70, 27.28, 24.18, −5.96. GC-MS m/z 266 (M⁺), 197.

Ph₂MeSi(CH₂)₃CH(CH₃)₂: NMR (o-C₆H₄Cl₂, 600.13 MHz): δ 7.76-7.75 (m, overlap with excess PhMeSiH₂), 7.51-7.48 (m, overlap with excess PhMeSiH₂), 1.71 (septet, J=6.6 Hz, 1H), 1.64 (m, 2H), 1.43 (m, 2H), 1.27 (m, 2H), 1.04 (d, J=7.2 Hz, 6H), 0.76 (s, 3H, overlap with excess PhMeSiH₂). $^{13}$C{$^1$H} NMR (o-C₆H₄Cl₂, 150.92 MHz): δ 137.58, 134.57, 129.19, 127.96, 43.14, 27.62, 22.67, 21.77, 14.45, −4.35. GC-MS m/z 267 ((M-CH₃)⁺), 204, 197.

(Me₃SiO)₂MeSi(cyclopentyl): $^1$H NMR (o-C₆H₄Cl₂, 600.13 MHz): δ 1.93-1.88 (m, 2H), 1.78-1.72 (m, 2H), 1.70-1.64 (m, 2H), 1.60-1.54 (m, 2H), 1.02 (m, 1H), 0.32 (s, 18H), 0.22 (s, 3H). $^{13}$C{$^1$H} NMR (o-C₆H₄Cl₂, 150.92 MHz): δ 27.59, 27.42, 27.12, 2.01, −1.61. GC-MS m/z 290 (M⁺), 275, 221, 207.

Ph₂ClSi(cyclopentyl): $^1$H NMR (o-C₆H₄Cl₂, 600.13 MHz): δ 7.86 (m), 7.55-7.50 (m, overlap with excess Ph₂ClSiH), 2.04 (m, 2H), 1.88 (m, 1H), 1.81-1.70 (m, 6H). $^{13}$C{$^1$H} NMR (o-C₆H₄Cl₂, 150.92 MHz): δ 134.67, 133.79, 130.45, 128.10, 28.06, 27.18, 25.94. GC-MS m/z 286 (M⁺), 217, 181.

PhSiH₂(cyclopentyl): $^1$H NMR (o-C₆H₄Cl₂): 4.53 (d), 2.02 (m), 1.76 (m), 1.68 (m), 1.57 (m), 1.41 (m). $^{13}$C{$^1$H}

NMR (C$_6$D$_5$Br, 150.92 MHz): δ 135.65, 132.72, 129.68, 128.16, 29.90, 27.17, 21.36. GC-MS m/z 176 (M$^+$), 148, 133, 120, 107, 98, 81, 67.

MesSiH$_2$(cyclopentyl): $^1$H NMR (o-C$_6$H$_4$Cl$_2$, 499.92 MHz): δ 4.62 (d), 2.61, 2.40, 2.00 (m), 1.81 (m), 1.69 (m), 1.57 (m), 1.43 (m). GC-MS m/z 218 (M$^+$), 150, 135, 119, 105.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A cationic compound which comprises a first row metal atom supported on a phosphorus-containing ligand, wherein said ligand has the formula:

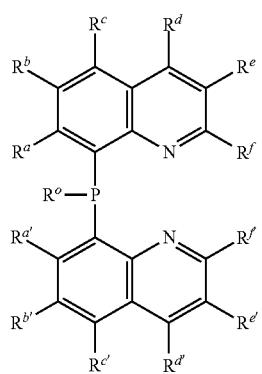

(II)

wherein

R$^o$ is a member selected from substituted or unsubstituted alkyl, substituted or unsubstituted heteroalkyl, substituted or unsubstituted aryl, substituted or unsubstituted heteroaryl and amine;

R$^a$, R$^b$, R$^c$, R$^d$, R$^e$, R$^f$, R$^{a'}$, R$^{b'}$, R$^{c'}$, R$^{d'}$, R$^{e'}$, and R$^{f'}$ are members independently selected from H, substituted or unsubstituted alkyl, substituted or unsubstituted heteroalkyl, halogen, CN, CF$_3$, acyl, —SO$_2$NR$^8$R$^9$, —NR$^8$R$^9$, —OR$^8$, —S(O)$_2$R$^8$, —C(O)R$^9$, —COOR$^8$, —CONR$^8$R$^9$, —S(O)$_2$OR$^8$, —OC(O)R$^8$, —C(O)NR$^8$R$^9$, —NR$^8$C(O)R$^9$, —NR$^8$SO$_2$R$^9$ and —NO$_2$, wherein two or more of R$^a$, R$^b$, R$^c$, R$^d$, R$^e$, R$^f$, R$^{a'}$, R$^{b'}$, R$^{c'}$, R$^{d'}$, R$^{e'}$, and R$^{f'}$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl wherein R$^8$ and R$^9$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and R$^8$ and R$^9$, together with the atoms to which they are bonded, are optionally joined to form a 5- to 7-membered ring.

2. The compound according to claim 1, wherein R$^o$ has the formula:

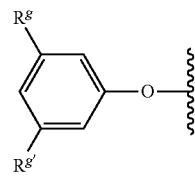

wherein

R$^g$ and R$^{g'}$ are members selected from H, substituted or unsubstituted alkyl, substituted or unsubstituted heteroalkyl, halogen, CN, CF$_3$, acyl, —SO$_2$NR$^{10}$R$^{11}$, —NR$^{10}$R$^{11}$, —OR$^{10}$, —S(O)$_2$R$^{10}$, —C(O)R$^{11}$, —COOR$^{10}$, —CONR$^{10}$R$^{11}$, —S(O)$_2$OR$^{10}$, —OC(O)R$^{10}$, —C(O)NR$^{10}$OR$^{11}$, —NR$^{10}$C(O)R$^{11}$, —NR$^{10}$SO$_2$R$^{11}$ and —NO$_2$, wherein two or more of R$^a$, R$^b$, R$^c$, R$^d$, R$^e$, R$^f$, R$^{a'}$, R$^{b'}$, R$^{c'}$, R$^{d'}$, R$^{e'}$, and R$^{f'}$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl wherein R$^{10}$ and R$^{11}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and R$^{10}$ and R$^{11}$, together with the atoms to which they are bonded, are optionally joined to form a 5- to 7-membered ring.

3. The compound according to claim 1, wherein said ligand has a formula which is a member selected from:

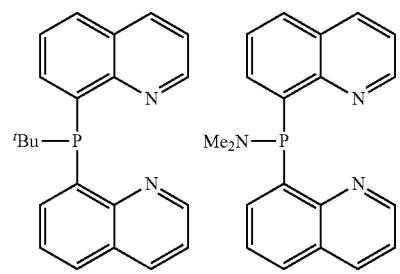

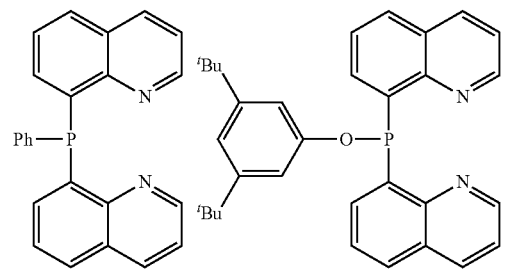

-continued

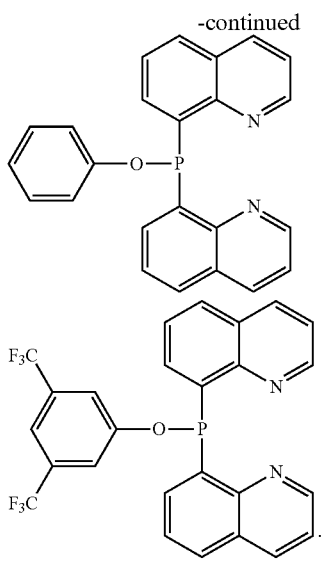

4. The compound according to claim 1, having the formula:

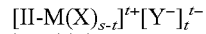

in which
II is said ligand, which has a structure according to Formula II;
M is said first row metal atom;
X is a ligand for said metal atom;
$Y^-$ is an anion; and
s and t are integers independently selected from 0, 1, 2, 3 and 4 and are selected such that s-t is 0, 1, 2 or 3.

5. The compound according to claim 1, wherein said compound catalyzes the addition of a hydrosilane across a pi-bonded system.

6. The compound according to claim 1, wherein said compound catalyzes the addition of a hydrosilane across a pi-bonded system which is a member selected from a double bond of an alkene and a triple bond of an alkyne.

7. The compound according to claim 1, wherein said first row metal atom is a member selected from a nickel atom, a copper atom, an iron atom and a cobalt atom.

8. A method of hydrosilylating a pi-bonded system, said method comprising: contacting said pi-bonded system with a compound according to claim 1, which is a catalyst for said hydrosilylating said system and a hydrosilane under conditions appropriate for said hydrosilylating.

9. A method of hydrosilylating a pi-bonded system, wherein said pi-bonded system is a member selected from an alkene, an alkyne, and a carbonyl, said method comprising: contacting said pi-bonded system with a compound according to claim 1, which is a catalyst for said hydrosilylating and a hydrosilane under conditions appropriate for said hydrosilylating.

10. The method according to claim 8, wherein said hydrosilane is a member selected from a primary, secondary and tertiary hydrosilane.

* * * * *